(12) United States Patent
Gouge et al.

(10) Patent No.: US 9,183,719 B2
(45) Date of Patent: Nov. 10, 2015

(54) HUMAN SAFETY INDICATOR

(75) Inventors: Charles Mack Gouge, Columbus, GA (US); Kenneth Armstrong, Cary, NC (US); Terrance Ransbury, Chapel Hill, NC (US); Robert Smith, Raleigh, NC (US); Darrel Self, Davidson, NC (US)

(73) Assignee: Safetyminded Holdings, Inc., Columbus, GA (US)

( * ) Notice: Subject to any disclaimer, the term of this patent is extended or adjusted under 35 U.S.C. 154(b) by 0 days.

(21) Appl. No.: 13/594,300

(22) Filed: Aug. 24, 2012

(65) Prior Publication Data

US 2013/0222139 A1    Aug. 29, 2013

Related U.S. Application Data

(60) Provisional application No. 61/526,937, filed on Aug. 24, 2011.

(51) Int. Cl.
| | |
|---|---|
| *G08B 23/00* | (2006.01) |
| *G08B 21/02* | (2006.01) |
| *A61B 5/01* | (2006.01) |
| *G01K 13/00* | (2006.01) |
| *A61B 5/0205* | (2006.01) |

(Continued)

(52) U.S. Cl.
CPC . *G08B 21/02* (2013.01); *A61B 5/01* (2013.01); *A61B 5/02055* (2013.01); *A61B 5/6801* (2013.01); *A61B 5/746* (2013.01); *G01K 13/002* (2013.01); *A61B 5/1118* (2013.01); *A61B 5/681* (2013.01); *A61B 5/6803* (2013.01); *A61B 5/7405* (2013.01); *A61B 5/7455* (2013.01); *A61B 5/7475* (2013.01); *A61B 2560/0431* (2013.01)

(58) Field of Classification Search
CPC combination set(s) only.
See application file for complete search history.

(56) References Cited

U.S. PATENT DOCUMENTS 3,678,751 A * 7/1972 Mead et al. ............... 338/28
4,151,831 A * 5/1979 Lester ..................... 600/549

(Continued)

FOREIGN PATENT DOCUMENTS

EP     1081479 A1 * 3/2001 ............ G01K 13/00
JP     2006070783 A * 3/2006

(Continued)

OTHER PUBLICATIONS

Gouge, Charles; U.S. Provisional Patent Application entitled: Human Safey Indicator, having U.S. Appl. No. 61/526,937, filed Aug. 24, 2011, 24 pgs.

(Continued)

*Primary Examiner* — Paul Obiniyi
(74) *Attorney, Agent, or Firm* — Taylor English Duma LLP

(57) ABSTRACT

A human safety system includes a circuit including a microcontroller and at least one power source; a probe in communication with the circuit; at least one use detector in communication with the circuit; and at least one alert indicator in communication with the circuit. A method of using a human safety device, the method includes initiating operation of the human safety device; arranging the human safety device in communication with skin; and monitoring the human safety device for alert indicators. A method of monitoring a user includes waking from sleep state; sensing at least one condition of the user; determining if the sensed condition is in a human condition; continuously monitoring the condition of the user; and, returning to sleep state when the user condition is outside of the human condition for an amount of time.

19 Claims, 19 Drawing Sheets

(51) Int. Cl.
*A61B 5/00* (2006.01)
*A61B 5/11* (2006.01)

(56) References Cited

U.S. PATENT DOCUMENTS

| | | | |
|---|---|---|---|
| 5,020,547 A * | 6/1991 | Strock | 128/891 |
| 5,235,217 A | 8/1993 | Kirton | |
| 5,441,476 A * | 8/1995 | Kitado et al. | 600/26 |
| 5,486,200 A * | 1/1996 | Lindemans | 607/5 |
| 6,426,719 B1 | 7/2002 | Nagareda et al. | |
| 6,615,706 B1 * | 9/2003 | Wu | 99/331 |
| 6,891,136 B2 * | 5/2005 | Bikovsky et al. | 219/528 |
| 7,087,075 B2 | 8/2006 | Briscoe et al. | 607/104 |
| 7,329,843 B2 * | 2/2008 | Bikhovsky et al. | 219/528 |
| 7,916,036 B1 * | 3/2011 | Pope et al. | 340/573.4 |
| 8,175,672 B2 * | 5/2012 | Parker | 600/344 |
| 2001/0029325 A1 * | 10/2001 | Parker | 600/344 |
| 2002/0061049 A1 * | 5/2002 | Adachi et al. | 374/208 |
| 2003/0167034 A1 | 9/2003 | Balding | |
| 2004/0004547 A1 | 1/2004 | Appelt et al. | |
| 2004/0026409 A1 * | 2/2004 | Bikhovsky | 219/527 |
| 2004/0064169 A1 * | 4/2004 | Briscoe et al. | 607/104 |
| 2004/0064171 A1 * | 4/2004 | Briscoe et al. | 607/104 |
| 2004/0116822 A1 | 6/2004 | Lindsey | |
| 2004/0122337 A1 * | 6/2004 | Nostro | 600/549 |
| 2004/0188185 A1 | 9/2004 | Pieper | |
| 2005/0278069 A1 * | 12/2005 | Bash et al. | 700/276 |
| 2006/0024852 A1 * | 2/2006 | Joshi et al. | 438/18 |
| 2006/0045167 A1 * | 3/2006 | Pawlenko et al. | 374/148 |
| 2006/0206177 A1 * | 9/2006 | Bikhovsky et al. | 607/96 |
| 2007/0150006 A1 * | 6/2007 | Libbus et al. | 607/2 |
| 2007/0239038 A1 * | 10/2007 | Nicolaescu et al. | 600/483 |
| 2007/0294233 A1 | 12/2007 | Sheu et al. | |
| 2008/0009691 A1 * | 1/2008 | Parker | 600/344 |
| 2008/0294126 A1 * | 11/2008 | Reuben | 604/304 |
| 2009/0112078 A1 | 4/2009 | Tabe | |
| 2009/0131165 A1 * | 5/2009 | Buchner et al. | 463/30 |
| 2009/0227924 A1 * | 9/2009 | Conrad et al. | 602/2 |
| 2010/0219956 A1 * | 9/2010 | Greco et al. | 340/586 |
| 2010/0283616 A1 | 11/2010 | Ruhs et al. | |
| 2011/0023874 A1 * | 2/2011 | Bath et al. | 128/202.22 |
| 2011/0026562 A1 | 2/2011 | Bernier et al. | |
| 2011/0071482 A1 * | 3/2011 | Selevan | 604/307 |
| 2011/0270368 A1 * | 11/2011 | Ginsburg et al. | 607/105 |
| 2012/0036623 A1 * | 2/2012 | Minogue | 2/463 |
| 2012/0048951 A1 * | 3/2012 | Kim et al. | 236/12.1 |
| 2012/0240918 A1 * | 9/2012 | Kirsch et al. | 126/263.01 |
| 2012/0293898 A1 * | 11/2012 | Chiang et al. | 361/78 |
| 2013/0005243 A1 | 1/2013 | Royston | |
| 2013/0234823 A1 * | 9/2013 | Kahn et al. | 340/3.1 |

FOREIGN PATENT DOCUMENTS

| | | | |
|---|---|---|---|
| JP | 2007260365 A * | 10/2007 | |
| WO | WO 9731249 A1 * | 8/1997 | G01K 1/02 |
| WO | WO 02084240 A1 * | 10/2002 | |
| WO | WO 2008156470 A1 * | 12/2008 | G08B 21/02 |

OTHER PUBLICATIONS

Gouge, Charles; U.S. Patent Application entitled: Human Safey Indicator, having U.S. Appl. No. 13/590,609, filed Aug. 21, 2012, 26 pgs.
Gouge, Charles Mack; Non-Final Office Action for U.S. Appl. No. 13/590,609, filed Aug. 21, 2012, mailed Mar. 31, 2014, 30 pgs.
Embedded Data Systems, OW-TEMP-xF-12x-Foil Tape Temperature Sensor, 2 pgs.
Gouge, Charles Mack; Final Office Action for U.S. Appl. No. 13/590,609, filed Aug. 21, 2012, mailed Oct. 22, 2014, 23 pgs.
Gouge, Charles Mack; Non-Final Office Action for U.S. Appl. No. 13/590,609, filed Aug. 21, 2012, mailed Jun. 17, 2015, 25 pgs.
Gouge, Charles Mack; Final Office Action for U.S. Appl. No. 13/590,609, filed Aug. 21, 2012, mailed Oct. 6, 2015, 23 pgs.

* cited by examiner

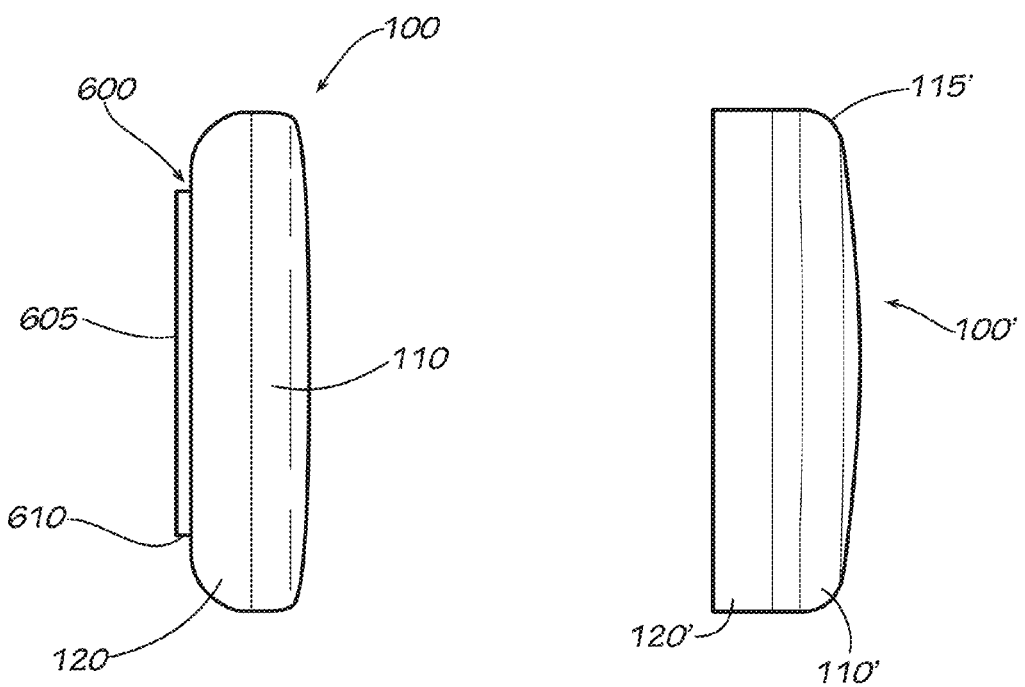
FIG. 7 FIG. 9
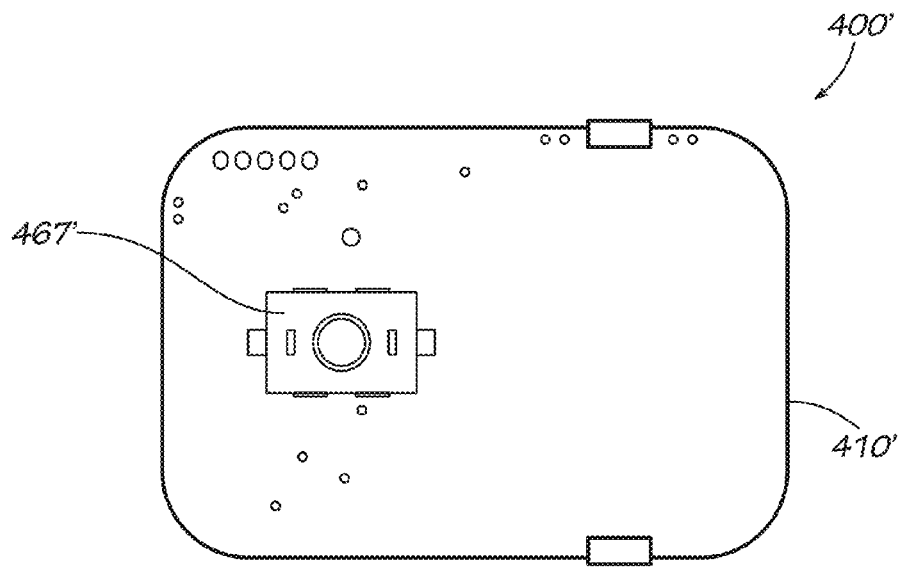
FIG. 10

SafetySpot Next State Table — 343

| Present State | Event | | | | | |
|---|---|---|---|---|---|---|
| | Button Press | Temp < $T_{BIO\ MIN}$ | $T_{BIO\ MIN} \leq$ Temp $< T_{RECOVERY}$ | $T_{RECOVERY} \leq$ Temp $< T_{OVERHEAT}$ | $T_{OVERHEAT} \leq$ Temp $< T_{BIO\ MAX}$ | Temp $\geq T_{BIO\ MAX}$ | Time to Sleep |
| Sleeping | Wakeup | --- | --- | --- | --- | --- | --- |
| Wakeup | Wakeup | Too Cold | Normal | Normal | Overheated | Too Hot | --- |
| Too Cold | Wakeup | Too Cold | Normal | Normal | Overheated | Too Hot | Sleeping |
| Normal | Wakeup | Too Cold | Normal | Normal | Overheated | Too Hot | --- |
| Overheated | Wakeup | Too Cold | Normal | Overheated | Overheated | Too Hot | --- |
| Too Hot | Wakeup | Too Cold | Normal | Normal | Too Hot Timeout | Too Hot | Sleeping |
| Too Hot Timeout | Wakeup | Normal | Normal | Normal | Normal | Normal | --- |

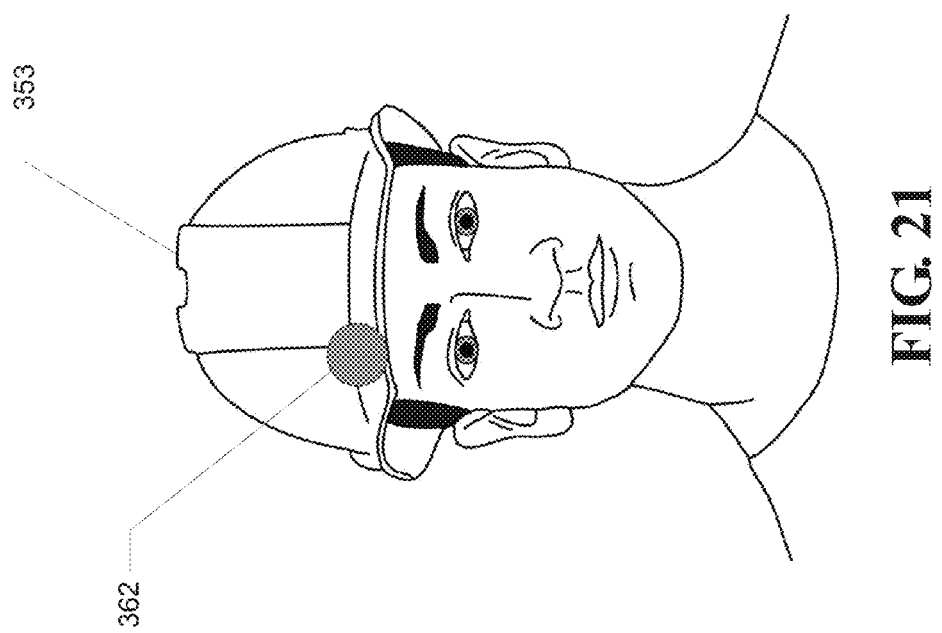

Sensor Indications — FIG. 22A

| Sounds | LEDs | Meaning |
|---|---|---|
| 🔊 (ascending) | (R)(Y)(G) | Ready for Use — 371 |
| 🔊 (descending) | (G)(Y)(R) | Going to Sleep — 372 |
| 🔊🔊 ×5 | (R) ×3 | Alert State — 373 |

FIG. 22A — 370

Troubleshooting Indications — FIG. 22B

| Sounds | LEDs | Meaning |
|---|---|---|
| 🔊🔊🔊 | (Y) ×3 | Low Battery: Replace Sensor — 376 |
| 🔊🔊 ×3 | (R) ×3 | Dead Battery: Do not use, replace Sensor — 377 |
| 🔊🔊🔊 | (R) ×3 | Temperature Out of Range: Press start button to reset Sensor — 378 |
| 🔊 | (R) ×5 | Temperature Sensor Error: Do not use, replace Sensor — 379 |

FIG. 22B — 375

HUMAN SAFETY INDICATOR

CROSS-REFERENCE TO RELATED APPLICATIONS

This application claims the benefit of U.S. Provisional Application 61/526,937 filed on Aug. 24, 2011, which is hereby incorporated herein in its entirety by reference.

FIELD

The present disclosure relates to temperature safety. More specifically, this disclosure relates to measuring and alerting human temperature.

BACKGROUND

Unsafe temperatures can lead to injury and even death in humans. Athletes, utility workers, construction workers, manufacturing workers, and hazardous-material workers are among those especially subjected to harsh temperatures, increasing the concerns for employers and schools on how to protect workers and athletes. Other individuals also may be subjected to dangerous overheating in some circumstances.

SUMMARY

A human safety system includes a circuit including a microcontroller and at least one power source; a probe in communication with the circuit; at least one use detector in communication with the circuit; and at least one alert indicator in communication with the circuit. A method of using a human safety device, the method includes initiating operation of the human safety device; arranging the human safety device in communication with skin; and monitoring the human safety device for alert indicators. A method of monitoring a user includes waking from sleep state; sensing at least one condition of the user; determining if the sensed condition is in a human condition; continuously monitoring the condition of the user; and, returning to sleep state when the user condition is outside of the human condition for an amount of time.

DESCRIPTION OF THE FIGURES

The features and components of the following figures are illustrated to emphasize the general principles of the present disclosure and are not necessarily drawn to scale. Corresponding features and components throughout the figures may be designated by matching reference characters for the sake of consistency and clarity.

FIG. 7 is an outer side view of the safety indicator of FIG. 1.

FIG. 9 is an outer side view of a safety indicator in accord with one embodiment of the current disclosure.

FIG. 10 is a front side view of a PCB assembly in accord with one embodiment of the current disclosure.

FIG. 19 is a state table illustrating a method of the safety indicator of FIG. 15A.

FIG. 21 is a diagram of a user wearing a helmet equipped with the safety indicator of FIG. 15A.

FIG. 22A is a sensor indication table in accord with one embodiment of the current disclosure.

FIG. 22B is a troubleshooting indication table in accord with one embodiment of the current disclosure.

DETAILED DESCRIPTION

In 2001, an NFL player died of heat stroke after a team practice. Between July and August, 2011, two high school football players in Georgia died from overheating. As illustrated by the two examples above, the problem of overheating has posed for years—and still poses—a grave threat to even the most well-conditioned athletes. Although a decade passed since the NFL player's death, no technology solution existed to prevent the overheating of the Georgia athletes. Utility workers, construction workers, and manufacturing and warehouse employees are also commonly exposed to risks associated with overheating. For many such workers, solutions available to athletes—such as changing practice locations to an air conditioned facility—simply are not available.

Moreover, individuals seeking to train outdoors are often exposed to the risk of heat-related injuries. Joggers, cross-trainers, cyclists, and even gardeners who spend prolonged amounts of time in hot outdoor weather are at risk for severe injury. Although an advanced heat safety system may be possible for certain workers and team athletes, individuals lack financial resources for such advanced systems.

Additionally, some systems monitor athletes and report data to a central location. However, the cost of such infrastructure is generally too high for small-scale use. Moreover, when errors occur with such systems, potential legal liability is placed on the monitoring party. For example, when a school adopts a system to monitor athletes' health during outdoor activity, a failure in that monitoring system could expose the school to liability for injuries occurring as a result of such failure.

Figure 1:
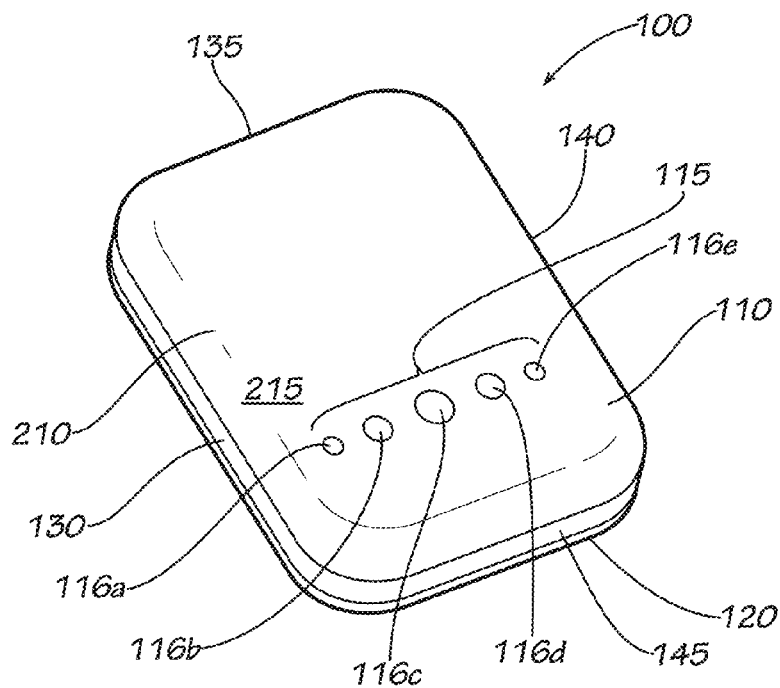
FIG. 1 is a perspective view of a safety indicator in accord with one embodiment of the current disclosure.

Disclosed is a human safety indicator for measuring and alerting a user's temperature. FIG. 1 displays a safety indicator 100. In various embodiments, the safety indicator 100 is attached to the inside of a user's hat, helmet, headband, or other headwear to provide a measurement of body temperature of the user. In other embodiments, the safety indicator 100 may be placed in contact with other body parts or otherwise in a position to measure the temperature of the user. The safety indicator 100 includes a front 110 and a back 120. The front 110 includes a temperature aperture 115 that is five holes 116a,b,c,d,e in the current embodiment, although other embodiments may include other shapes or combinations of temperature aperture 115 styles. As can be seen in the view of FIG. 1, the safety indicator 100 is generally rectangular in the current embodiment, although other embodiments may include other shapes. The front 110 includes a left side 130, a top side 135, a right side 140, a bottom side 145, an outside 210, and an inside 220 (not shown). An outside surface 215 is also shown. All references to "left" and "right" in this disclosure refer to the left and right directions when viewing the front 110 from the outside 210 with the top side 135 up and the bottom side 145 down. The front 110 has a cambered profile.

Figure 2:
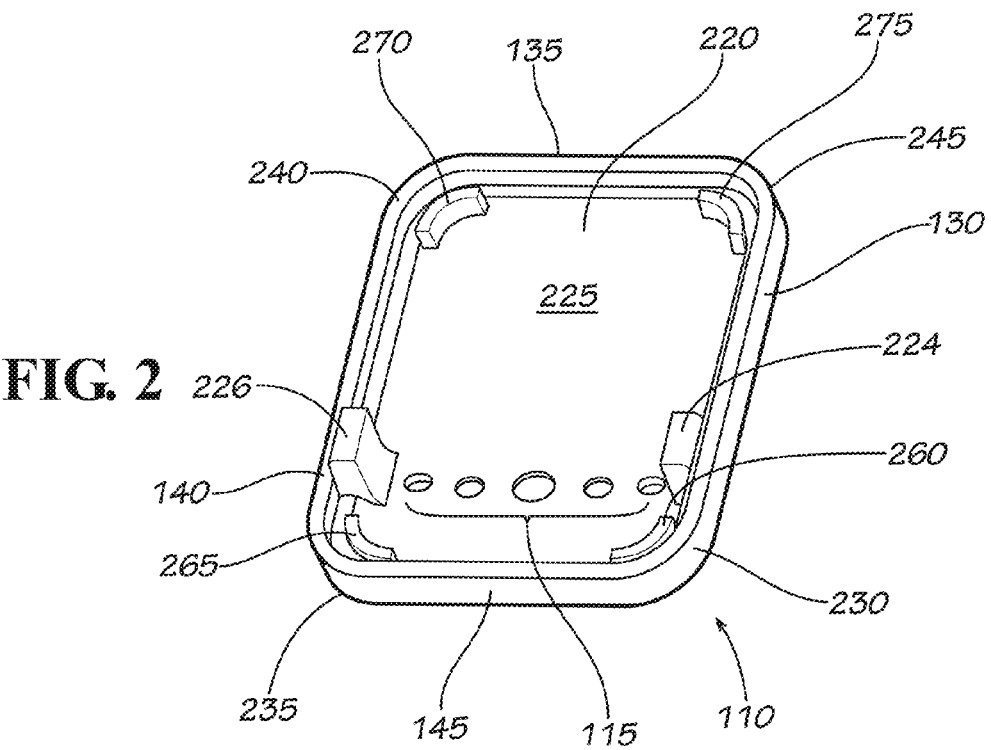
FIG. 2 is a perspective view of an inside of a front of the safety indicator of FIG. 1.

FIG. 2 displays the front 110 from an inside view. The inside 220 includes temperature probe holders 224,226. Rounded corners 230, 235, 240, 245 connect the sides 130, 135, 140, 145. An inside surface 225 is shown. Four shoulders 260, 265, 270, 275 extend from the inside surface 225. A temperature probe (not shown) is positioned between the temperature probe holders 224,226 in the current embodiment. In the current embodiment, the temperature probe is a metal tape. The metal tape temperature probe may be aluminum or copper in various embodiments. Other materials may be used in other embodiments as well. In various embodiments, other temperature probes may be used, including thermocouples, thermistors, and mercury thermometers, among others. In the current embodiment, the metal tape temperature probe is placed proximate the temperature aperture 115. In various embodiments, the front 110 or the back 120 may be made of metal, and one or both of the front 110 or the back 120 may serve as the temperature probe.

Figure 3:
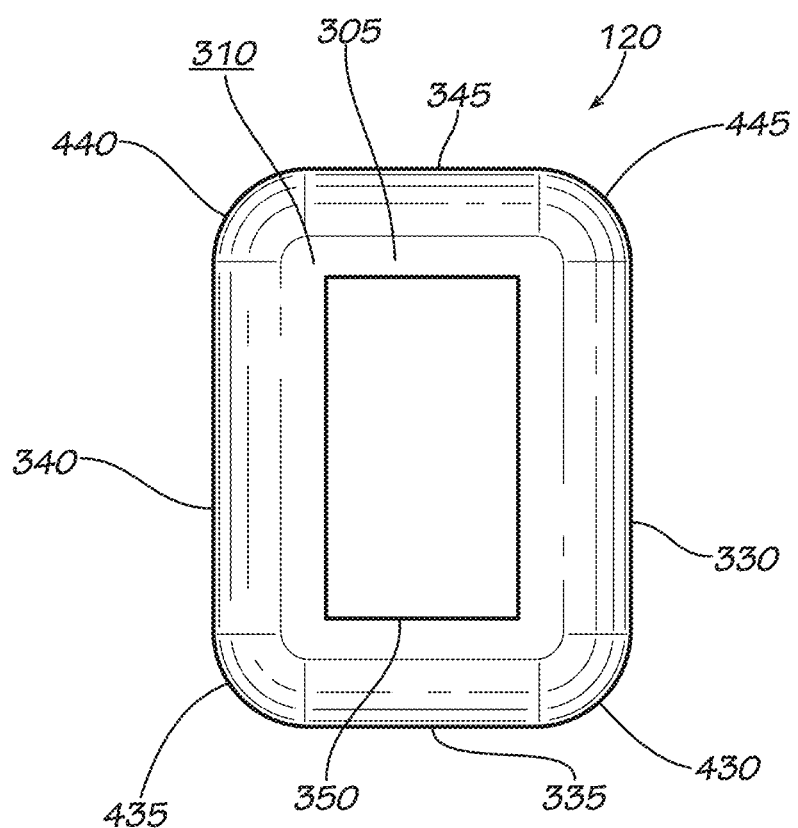
FIG. 3 is an outer side view a back of the safety indicator of FIG. 1.

FIG. 3 shows an outside view of the back 120. The back 120 includes an outside 305 and an inside (not shown). An outside surface 310 is shown on the outside 305. The back 120 includes a left side 330, a top side 335, a right side 340, a bottom side 345, and an inside 320 (not shown). Rounded corners 430, 435, 440, 445 connect the sides 330, 335, 340, 345. The back 120 defines a contact hole 350 that is rectangular in shape in the current embodiment, although other shape contact holes may be used. In some embodiments, no contact hole is needed. Each of the sides 330, 335, 340, 345 and the corners 430, 435, 440, 445 are filleted in the current embodiment. In various embodiments, the sides 330, 335, 340, 345 and the corners 430, 435, 440, 445 may be various shapes.

Figure 4:
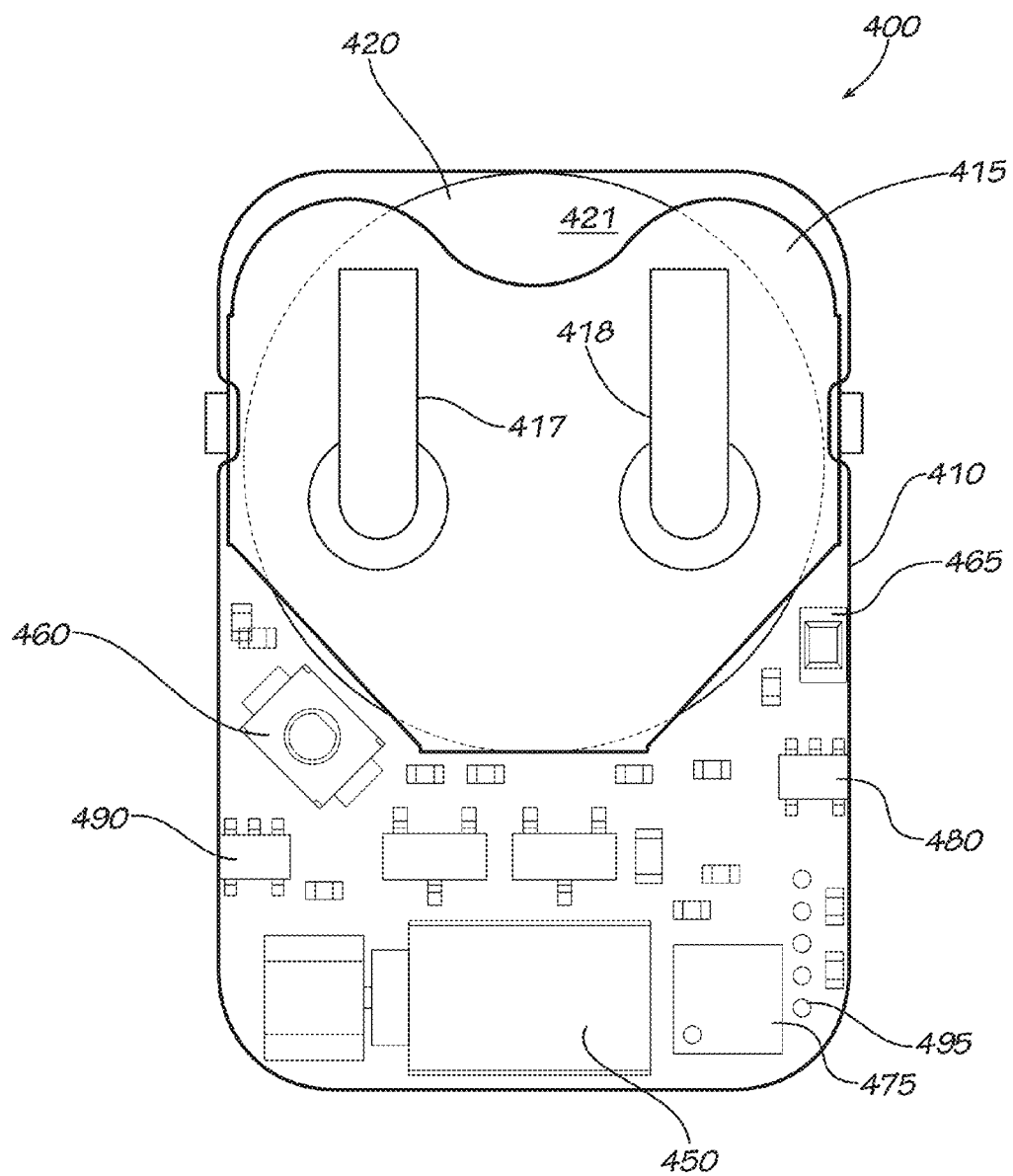
FIG. 4 is a back side view of a PCB assembly of the safety indicator of FIG. 1.

The safety indicator 100 includes a printed circuit board assembly 400 (PCB assembly) as seen in FIG. 4. The PCB assembly 400 includes a printed circuit board (PCB) 410 and a battery 420. A battery plate 415 holds the battery 420 in electrical contact with the PCB 410. The battery plate 415 includes two metal contacts 417,418 that contact the top surface 421 of the battery 420, which is the positive side of the battery 420 in the current embodiment. A portal 495 will be discussed later with reference to FIG. 13.

The PCB assembly 400 includes an alert indicator 450 and a use detector 460. In the current embodiment, the use detector 460 is a pressure sensor. The use detector 460 pressure sensor of the current embodiment is a button that may be pushed in order to detect use of the safety indicator 100. Pressure is applied to the use detector 460 pressure sensor by a button. Although the use detector 460 pressure sensor is shown on one side of the PCB 410, it may be in other places in various embodiments, including other physical locations on the PCB 410 or on the other side of the PCB 410. In other embodiments, the use detector 460 may be another type of device sufficient to determine whether the device is in use; in various embodiments, a photoelectric sensor or ambient light sensor may be used; in various embodiments, an ambient temperature sensor may be used to determine when there is a difference between the ambient temperature and the sensed temperature. In various embodiments, the temperature probe may be used as a conductivity loop to function as the use detector 460 based on electrical capacitance of touch. In various embodiments, the front 110 and back 120 may be made of conductive material, for which the front 110 and back 120 may serve as a conductivity loop to function as the use detector 460. If a conductivity loop is used, a pressure sensor may not be necessary or may be included as a redundancy. In various embodiments, multiple sensor types may be combined together to provide redundancy for the use detector 460. In the current embodiment, a use detector 465 is included to be a redundancy to use detector 460. The use detector 465 in the current embodiment is an ambient light sensor or photoelectric sensor. As such, the safety indicator 100 of the current embodiment includes two methods of determining when the safety indicator 100 is in use. In various embodiments, the use detector 460 may be activated by the flexure of the casing, particularly of the back. In various embodiments, the first activation of any use detector 460,465 may provide the activation of the safety indicator 100.

In the current embodiment, the alert indicator 450 is a vibration motor. In various embodiments, the alert indicator 450 may be other types of indicators, for example, a speaker, a light, temperature-sensitive color-shifting material, or a wireless signal among other types of indicators. Moreover, there may be various types of indicators for each method. For example, an alert indicator 450 vibration motor may be a DC motor, a stepper motor, a solenoid, or any other system configured to provide vibration through electromotive force. Similarly, an alert indicator 450 light may be an incandescent light, an LED (light emitting diode), or a display, among others embodiments.

The PCB assembly 400 also includes two temperature sensors 480,490. The two temperature sensors are implemented for redundancy to ensure accuracy of the measured temperature. In various embodiments, one temperature sensor may be used. In various other embodiments, more than two temperature sensors may be used. In variations of the current system, the temperature sensors may be altered or combined with additional sensors to sense other human functions including blood pressure, heart rate, and caloric data, among others. A microcontroller 475 is included in the PCB assembly 400. In the current embodiment, the microcontroller 475 is a Microchip PIC, although other microcontrollers 475 may be used in various embodiments, including ICs, other microchip, microprocessors, and other electronic circuitry, among others.

It should be noted that other features of the PCB assembly 400 are shown but not referenced. These features should not be considered limiting on the disclosure but are provided for a full disclosure. Such features may be referenced in later documents flowing from this disclosure; however, no single feature should be considered limiting on the breadth or scope of claimable disclosure.

Figure 5:
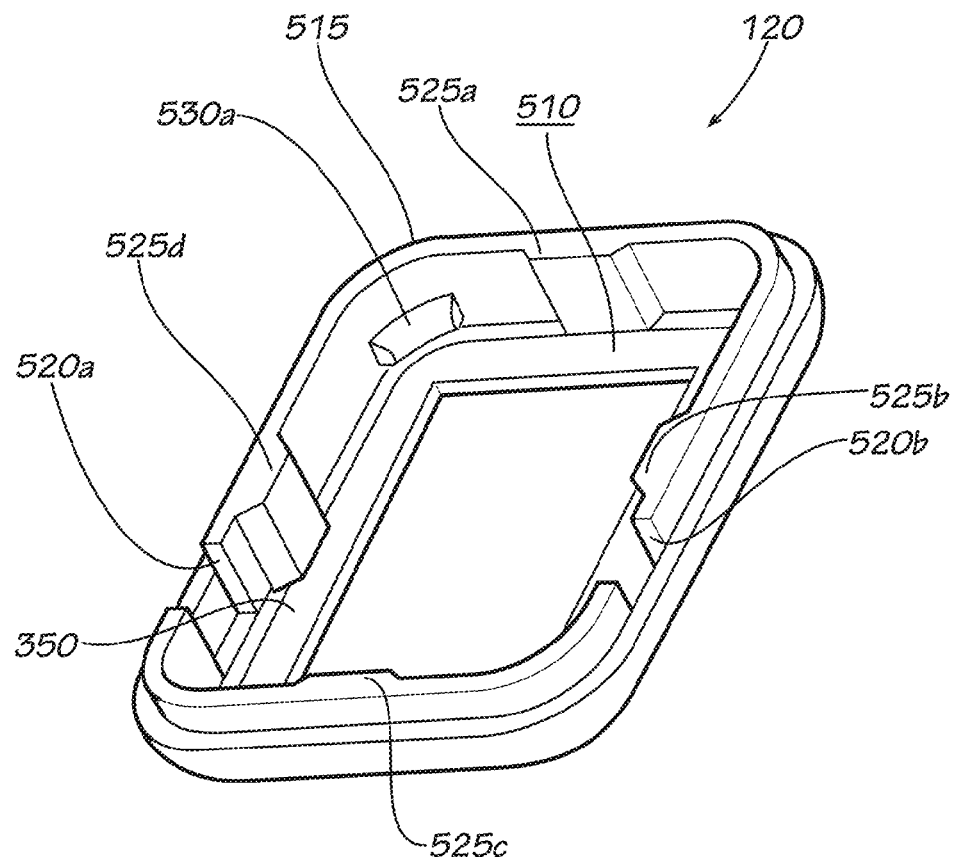
FIG. 5 is an inside perspective view of the back of FIG. 3.
Figure 12:
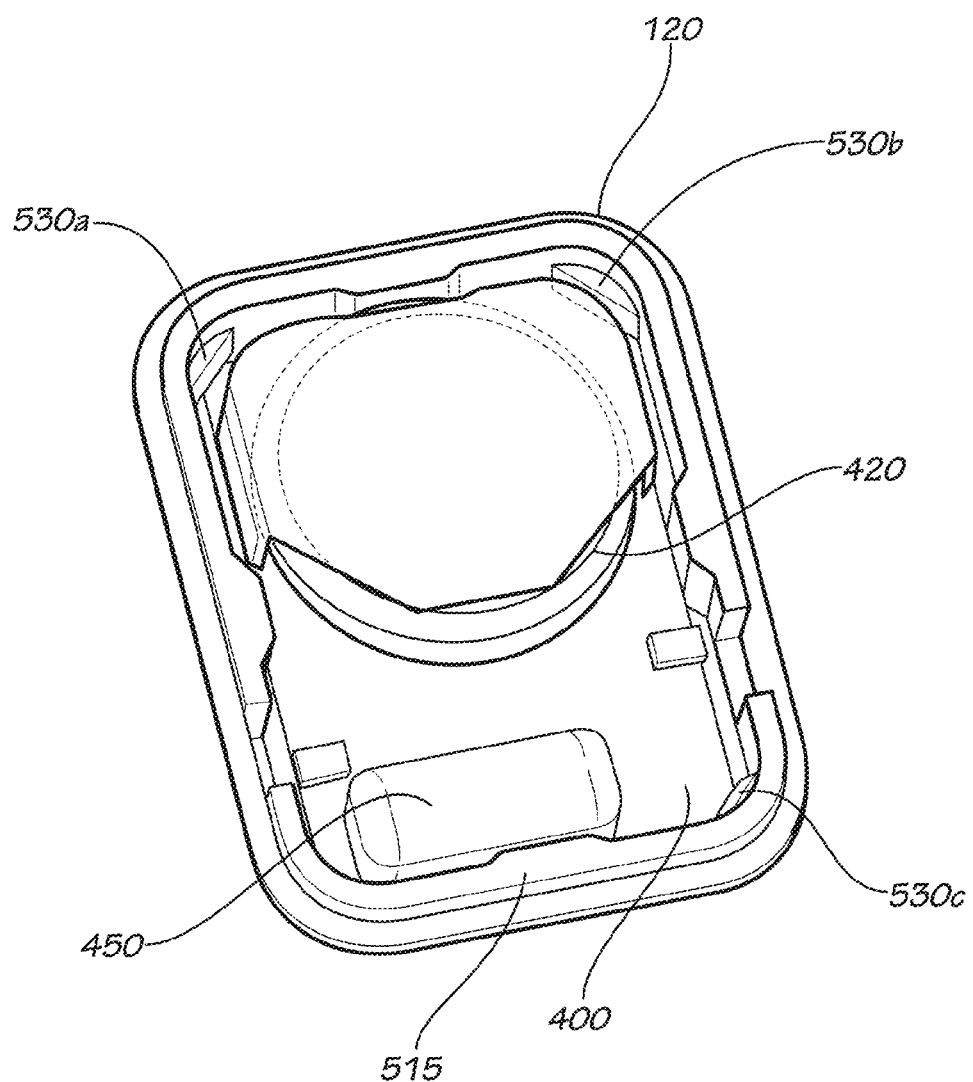
FIG. 12 is an inside perspective view of the PCB assembly of FIG. 4 together with the back of FIG. 3.

FIG. 5 shows an inside perspective view of the back 120. The inside surface 510 of the back includes multiple features. A weld shoulder 515 follows the perimeter of the back 120 providing a weld interface with the front 110. The weld shoulder 515 includes two holder pockets 520a,b so that the temperature probe holders 224,226 may be fit into the back without interference. The back 120 includes several locating bosses 525a,b,c,d located on the inside surface 510 at each side of the weld shoulder 515 to locate the PCB 410 and, thereby, the PCB assembly 400. Also, locking tabs 530a (530b,c,d not shown) are located at the corners of the inside of the weld shoulder 515 to hold the corners of the PCB 410. The interaction of the PCB assembly 400 and the back 120 is shown in FIG. 12.

Figure 6:
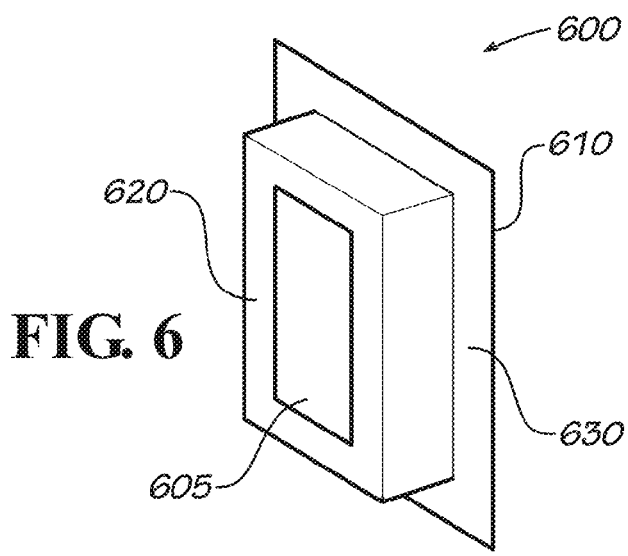
FIG. 6 is a perspective view of a pressure button assembly of the safety indicator of FIG. 1.

FIG. 6 shows a pressure button assembly 600 which includes a pressure button 610 and a connection pad 605. In the current embodiment, the connection pad 605 is a glue pad. In other embodiments, the connection pad 605 may be other affixing means, such as Velcro, variations of Velcro, tape, magnets, or, among others, mechanical affixing means such as mechanical winged tabs, clips, fingers, and other mechanical affixing means. The pressure button 610 has a button portion 620 and a flange portion 630. The button portion 620 is sized so that it may occupy the space provided by the contact hole 350. The flange portion 630 is sized larger than the contact hole 350 so that it may retain the pressure button 610 inside the safety indicator 100.

As seen in FIG. 7, when the safety indicator 100 is assembled, the front 110 and the back 120 are placed together. The front 110 and the back 120 are ABS plastic in the current embodiment, although other material choices may be used in other embodiments, including silicone, metal, other plastics, wood, resin, epoxy, foam, rubber, and other materials. In the current embodiment, the front 110 and back 120 are plastic welded to prevent the introduction of contaminants at the border, such as water or sweat. The metal tape temperature probe (not shown) is attached to the inside of the front 110. The PCB assembly 400 is placed such that the temperature probe is between the front 110 and PCB assembly 400. The pressure button assembly 600 is then placed between the PCB assembly 400 and the back 120, wherein the back 120 and front 110 together enclose the temperature probe, the PCB assembly 400, and the pressure button assembly 600. While the pressure button assembly 600 is captured, only the flange portion 630 is restricted, as the button portion 620 and connection pad 605 protrude through the contact hole 350, as shown. The pressure button assembly 600 is aligned such that any pressure on the pressure button assembly 600 will push the pressure button assembly 600 into the use detector 460, which is a pressure sensor in the current embodiment. When the use detector 460 pressure sensor is pressed, it senses that pressure has been applied and thereby that the safety indicator 100 is ready for use. In the current embodiment, the second use detector 465 is an ambient light sensor. It detects use whenever the light sensor is covered or in the shadows. In the current embodiment, both are activated to allow the safety indicator 100 to begin measuring the user's temperature. In various other embodiments, one use detector 460,465 may be used and may be of any variety of sensor. In various other embodiments, no use detector 460,465 will be included, and the safety indicator 100 will be continuously on.

In various embodiments, functions of the use detector 460, 465 are performed through electronic switching. For example, in one embodiment, use detection occurs based on the temperature that is sensed. The safety indicator 100 remains in sleep state so long as the sensed temperature remains below a "human condition," which occurs at human body temperature (98.6 degrees Fahrenheit). The human condition that is sensed may be adjusted for heat conductivity of the materials of the safety indicator 100. In the current embodiment, the adjustment is approximately three degrees Fahrenheit, so the human condition occurs at a sensed temperature of about 95 degrees Fahrenheit as correlated to a human body temperature of about 98.6 degrees Fahrenheit. Once the safety indicator 100 determines that it is in the human condition, it awakens from sleep state to operation, wherein it provides an indication that it is awake—in the current embodiment, one vibration, although a different number of vibrations may be used in other embodiments as well as other indication methods including lights, sounds, and other sensations, among other indication methods. The safety indicator 100 remains in operation until the sensed temperature falls below 93 degrees Fahrenheit, at which point the safety indicator 100 determines that it is no longer in the human condition and likely not in use by a human.

Once assembled, the safety indicator 100 is prepared for use. For control of battery life, the safety indicator 100 is packed in a sleep mode and is not using substantial battery power. As stated previously, the safety indicator 100 of the current embodiment is intended to be affixed to the user's hat, helmet, headband, or other headwear to provide a measurement of body temperature of the user. The connection pad 605 in the current embodiment is a glue pad, which is supplied to the user with a backing. Upon receiving the safety indicator 100, the user removes the backing and presses the connection pad 605 against the inside of the user's headwear in a location to contact the user's temple. When the user applies pressure to the safety indicator 100 to seat the connection pad 605 glue against the headwear, the use detector 460 is activated by the pressure. This activation is the first activation of the safety indicator 100 and begins an internal clock (not shown). If no use detector 460 pressure sensor is included, the function can be performed by other types use detectors. One of skill in the art will understand some changes in methodology may need to be implemented in order to support changes in the type of use detector implemented.

In the current embodiment, when the use detectors 460,465 are not activated, the safety indicator 100 is in sleep mode and is not measuring temperature. The sleep mode uses little electrical energy of the battery 420. However, when the use detectors 460,465 are activated by pressure and light, respectively, the safety indicator 100 is in operation, actively measuring temperature and using substantially more electrical energy of the battery 420. When one of the use detectors 460,465 becomes inactive, the safety indicator 100 returns to sleep mode until it may be activated again.

It is understood that the battery life of the safety indicator 100 is unknown and depends greatly on the amount of use in operation. The user may be exposed, thereby, to an unsafe condition if he is actively using a safety indicator 100 with a weak battery 420 or with poor battery life. As such, it is a safety feature of the current embodiment to deplete any remaining electrical energy stored in the battery 420 at the expiration of one year from the activation of the safety indicator 100. When the internal clock reaches one year, the safety indicator 100 permanently activates to operation and does not return to sleep mode. The battery 420 depletes, and the safety indicator 100 should be disposed by the user. In the current embodiment, the alert indicator 450 activates to deplete the battery 420.

In operation, the safety indicator 100 operates by measuring temperature using the temperature probe. The temperature probe measures temperature at the user's temple when the safety indicator 100 is in contact or proximate to the user's temple. A user temperature is gained using the average (mean) value of the two temperature sensors 480, 490, which are measuring from the same temperature probe. The averaging to determine user temperature provides validation against false readings, as the redundancy ensures that correct values will be determined.

The safety indicator 100 will include a maximum user temperature and a minimum user temperature. The maximum user temperature and minimum user temperature are programmable. Moreover, the user temperature that is sensed is a skin-level temperature; as previously described, the skin-level temperature is adjusted to correlate for the difference between skin temperature in the temporal region and core body temperature. The adjustment needed is approximately 3.2 degrees Fahrenheit. Should the user temperature exceed the maximum user temperature or fall below the minimum user temperature, the alert indicator 450 will activate, identifying a problem to the user. In the current embodiment, the activation of the alert indicator 450 is by means of a vibration motor turning on, thereby causing the safety indicator 100 to vibrate. The user feels the vibration of the safety indicator 100, thereby noticing that his or her temperature has exceeded the maximum user temperature or fallen below the minimum user temperature, for which the user should seek aid. In some embodiments, the maximum user temperature is 102.5 degrees Fahrenheit.

In some embodiments, safety indicators 100 may be integrated into a network for reporting such temperature data to a central location, to a wireless computer, or otherwise to a network. The current embodiment does not report such data to a central location but instead relies on the user to self-report his or her temperature safety.

The method as described above is shown in FIG. 8. Initial activation of the use detector 460 activates the safety indicator 100 as shown in step 805. Immediately following activation, the internal clock starts as in step 810, from which one year will be determined. Sleep mode 815 is indicated by the dotted line box called out in the flow diagram. The sleep mode 815 includes first step 820, wherein the internal clock is checked to ensure that less than one year has passed since activation, followed by step 825, wherein both use detectors 460, 465 are checked to determine whether to remove the safety indicator 100 from sleep mode 815. If both use detectors 460, 465 are activated, the safety indicator 100 goes into operation 830 as denoted by the dotted line box.

In operation 830, the user's body heat is transmitted into the temperature probe as indicated in step 835. The temperature of the temperature probe is measured by the temperature sensors 480, 490 in parallel as indicated in steps 840 and 845. The measured values of the temperature sensors 480, 490 are averaged as in step 850 to determine the user temperature. The user temperature is compared to the maximum and/or the minimum allowable user temperatures as shown in step 855.

Regarding step 855, in most cases, the user temperature will fall within the allowable temperature range. If so, the flow diagram proceeds to reevaluate whether both use detectors 460, 465 remain activated, as shown in step 870. If both use detectors 460, 465 are still activated, the flow diagram loops to step 835. If one or more of the use detectors 460, 465 is not activated, the flow diagram leaves operation 830 and returns to step 820 in sleep mode 815.

On the other hand, if step 855 determines that the user temperature is outside of the allowable range, the flow diagram proceeds to activate the alert indicator 450 as shown in step 860. In the current embodiment, the alert indicator 450 remains active until the battery 420 loses all electrical charge and dies, as indicated by step 865. In various embodiments, the alert indicator 450 may be permitted to deactivate if the user temperature returns to the allowable range. The alert indicator 450 may include a series of vibrations in various embodiments, of which one example can be seen in FIG. 11.

As described previously, the electrical energy stored in the battery 420 is depleted at the expiration of one year from the activation of the safety indicator 100. As shown by step 820, reading of the internal clock is performed many times over the life of the safety indicator 100. If the internal clock indicates that the safety indicator 100 has been active for over one year, step 820 bypasses all remaining steps in the flow diagram, proceeding to activate the alert indicator 450 as shown in step 860 until the battery 420 dies as indicated by step 865. This battery 420 depletion process will occur regardless of whether the user temperature is within or is outside of the allowable range. One of skill in the art will understand variations on this methodology will be supported by variations in flow of the method and will depend on which hardware is implemented into each embodiment safety indicator 100.

FIG. 9 displays another embodiment of a safety indicator 100'. As can be seen, the safety indicator 100' includes a front 110' and a back 120'. The front 110' is cambered much like the front 110 but includes rounded edges 115'. The back 120' does not include any rounded edges as does the back 120.

FIG. 10 displays another embodiment of a PCB assembly 400'. In the current embodiment, the PCB assembly 400' has a use detector 467' located on a side of the PCB 410' opposite to the other use detectors 460, 465. The use detector 467' is a pressure sensor in the current embodiment. The use detector 467' provides a second-level redundancy in the current embodiment to ensure that that safety indicator 100 is not activated unless it is in use by a user.

Figure 11:
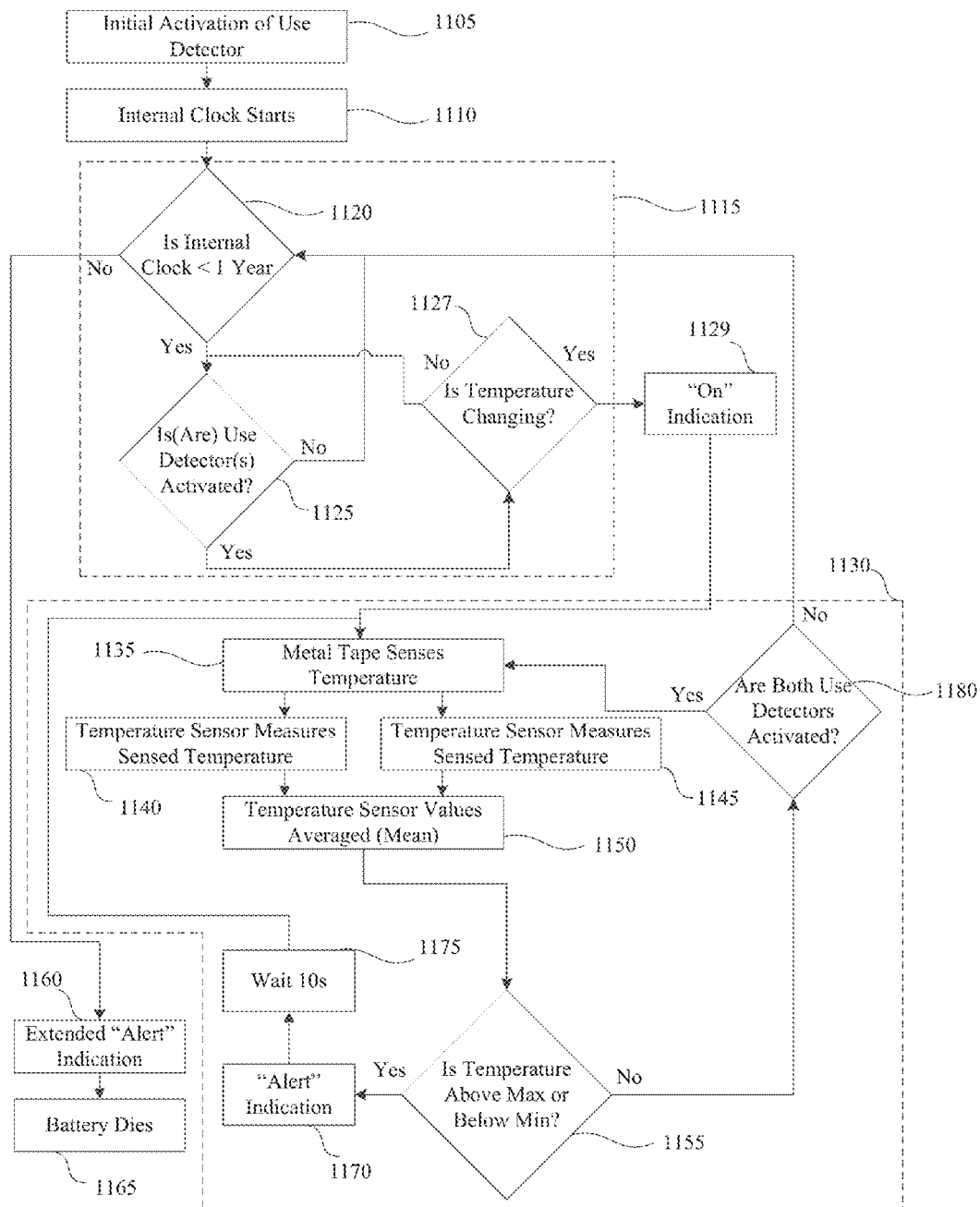
FIG. 11 is a flow diagram illustrating a method in accord with one embodiment of the current disclosure.

Another embodiment of a method is described in FIG. 11. The method begins similarly to the method of FIG. 8, wherein the initial action of the use detector 460 as shown in step 1105 causes the internal clock to start as shown in step 1110 followed by testing whether the internal clock is less than one year as indicated in step 1120 and then determining whether both use detectors are activated in step 1125. However, sleep mode 1115 differs from sleep mode 815 in that it includes a step 1127 to check whether the temperature is changing. If not, the method stays in sleep mode 1115 as indicated. If so, the method proceeds to step 1129 wherein an "on indication" is given to alert the user that the safety indicator 100 is going into operation 1130. In the current embodiment, the on indication is a single vibration produced by the alert indicator 450 vibration motor.

When the safety indicator 100 is in operation 1130, the temperature probe receives heat from the user's body as shown by step 1135. In steps 1140 and 1145, the temperature sensors 480, 490 measure heat sensed from the temperature probe. The values of the temperature sensors 480, 490 are averaged in step 1150 to achieve a user temperature, and the user temperature is compared to the maximum and minimum allowable user temperature in step 1155.

Figure 8:
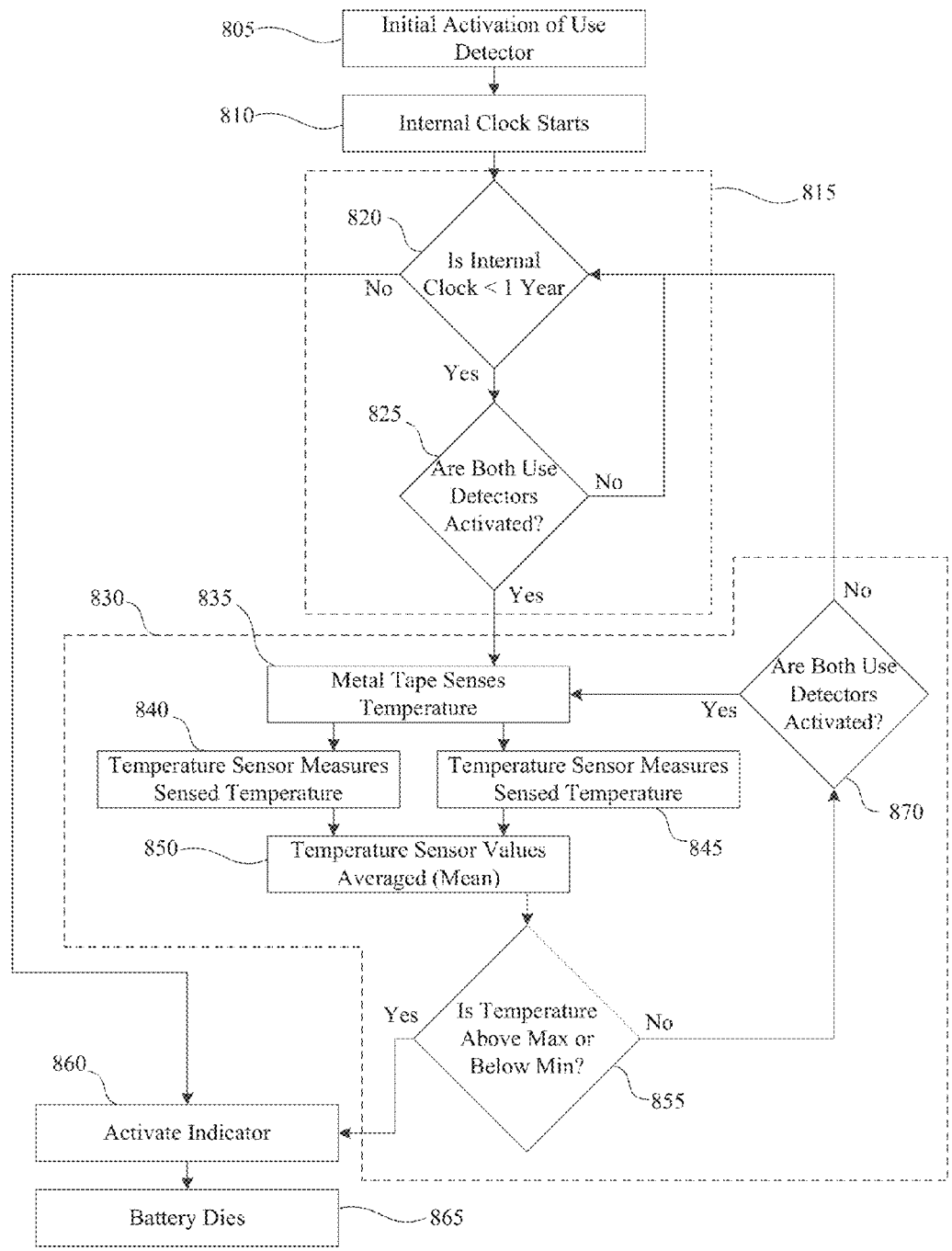
FIG. 8 is a flow diagram illustrating a method in accord with one embodiment of the current disclosure.

As with the method of FIG. 8, in most scenarios, the user temperature will be within the allowable range when compared by step 1155. In such a case, the flow diagram proceeds to step 1180 to determine if the use detectors 460, 465 are still activated. If so, the flow diagram loops to step 1135. If not, the flow diagram returns to sleep mode 1115 at step 1120.

However, if the user temperature is out of the allowable range as determined by step 1155, an "alert indication" is produced by the alert indicator 450 as shown in step 1170. In the current embodiment, the alert indication is four consecutive vibrations. Following the alert indication, the flow diagram proceeds to step 1175 to wait ten seconds before restarting the method of operation and, potentially, re-alerting the user if his or her temperature remains outside of the allowable range. In various embodiments, the waiting periods may be longer or shorter. Following step 1175, the flow diagram returns to step 1135.

In another embodiment, the method of FIG. 11 may be modified to produce one alert indication when the user temperature falls outside of the acceptable range but to wait 45 seconds before re-alerting the user so that the user temperature may fall back within the acceptable range. If the user temperature does not fall back within the acceptable range, the alert indications continue on a 10-second interval as described above.

As with the method of FIG. 8, an added safety feature allows the battery 420 to be depleted upon the expiration of one year. If the internal clock is greater than one year as compared in step 1120, the flow diagram proceeds to an "extended alert indication" as shown in step 1160 wherein the alert indication continues for an extended period of time until the battery 420 is exhausted of electrical charge, as shown in step 1165.

In some embodiments, the safety indicator 100 may be configured to disregard temperature readings in excess of 105.0 degrees Fahrenheit as a non-human temperature reading. This reading is termed a lockout threshold. In some embodiments, the temperature sensors 480,490 may be programmed to calibrate for a minimum of 60 seconds before triggering an alert.

In some embodiments, a sensed temperature that exceeds the lockout threshold may decrease when the safety indicator 100 comes in contact with the user. For example, if a safety indicator 100 is exposed to solar radiation for an extended amount of time, the sensed temperature may exceed 105.0 degrees Fahrenheit. When the user applies the safety indicator 100, the sensed temperature will decrease because the user's temple will be at a temperature below 105.0 degrees Fahrenheit. In such cases, the safety indicator 100 may be configured to disregard temperature readings in excess of 102.5 degrees Fahrenheit—those that would normally trigger an alert—until the user temperature is sensed below 102.5 degrees Fahrenheit.

In other embodiments, the safety indicator 100 will be configured to delay any alert for 60 seconds when the safety indicator 100 leaves the lockout threshold, allowing the safety indicator 100 time to measure a true user temperature.

As shown in FIG. 12, the PCB assembly 400 is inserted into the back 120 so that corners of the PCB assembly 400 are locked behind the locking tabs 530*a*,*b*,*c* (530*d* not shown). The placement of the battery 420 and the alert indicator 450 can be seen with respect to the back 120. In the current embodiment, the alert indicator 450 includes a protective cover. Other features of the PCB assembly 400 are obstructed from view in the current embodiment.

Figure 13:
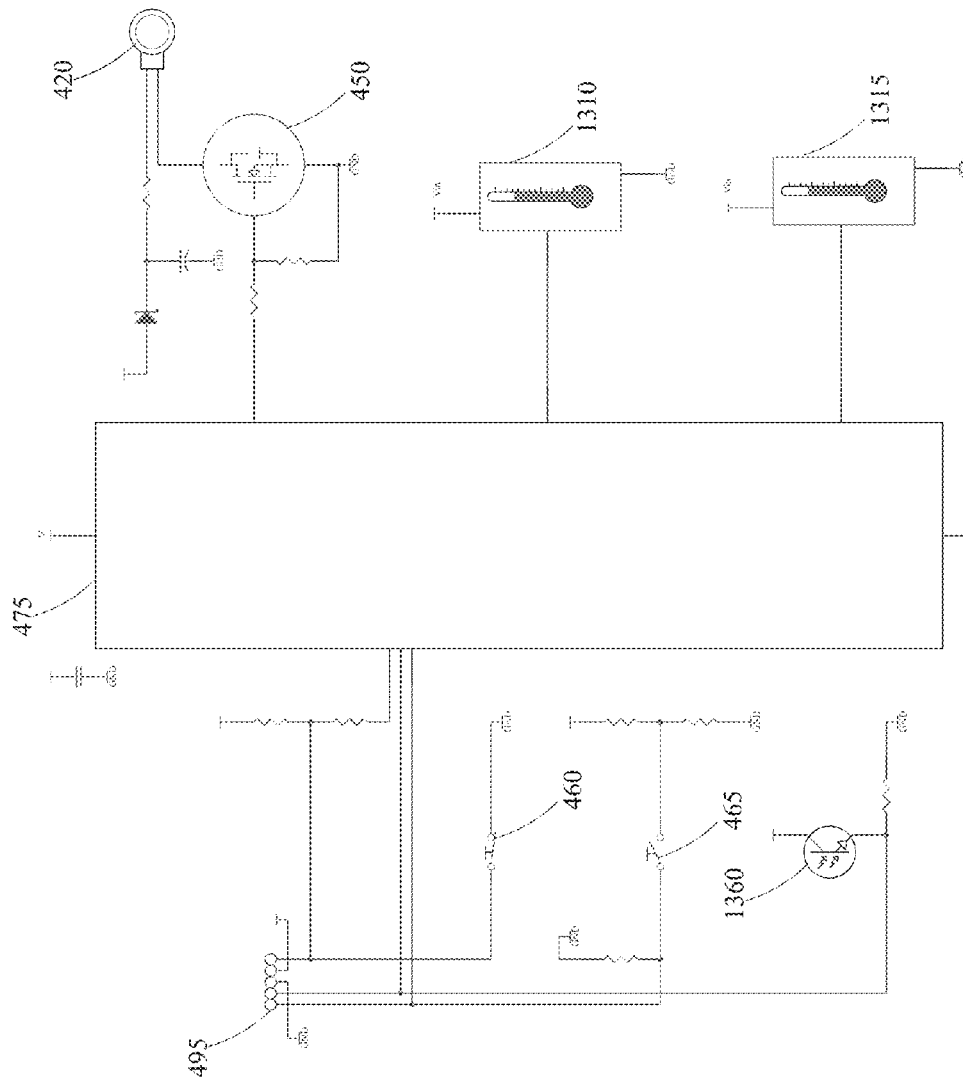
FIG. 13 is a schematic a safety indicator in accord with one embodiment of the current disclosure.

FIG. 13 shows a schematic of one embodiment of a safety indicator 1000. The use detector 460 is connected to the temperature sensors 480,490. The alert indicator 450 vibration motor is connected to the circuit as is the battery 420. The safety indicator 1000 of the current embodiment includes two use detectors 460,465 that are pressure sensors as well as a use detector 1360 that is an ambient light sensor. In the current embodiment, all use detectors 460,465,1360 must be activated to remove the safety indicator 1000 from sleep mode and place it in operation. The use detectors 460,465,1360 are connected to pins of the microcontroller 475. Temperature sensors 1310,1315 are connected to pins of the microcontroller 475. A pin of the microcontroller 475 is connected to the alert indicator 450 vibration motor. Although the control circuitry is powered by the battery 420, the alert indicator 450 is shown with a direct connection to the battery 420. A portal 1395 is also shown as included to allow connection for testing and for programming, although such portal 1395 is not available to the user in the current embodiment. Other circuitry and features are shown but not referenced or are not shown. However, supporting circuitry would be understood by one of skill in the art.

Figure 14:
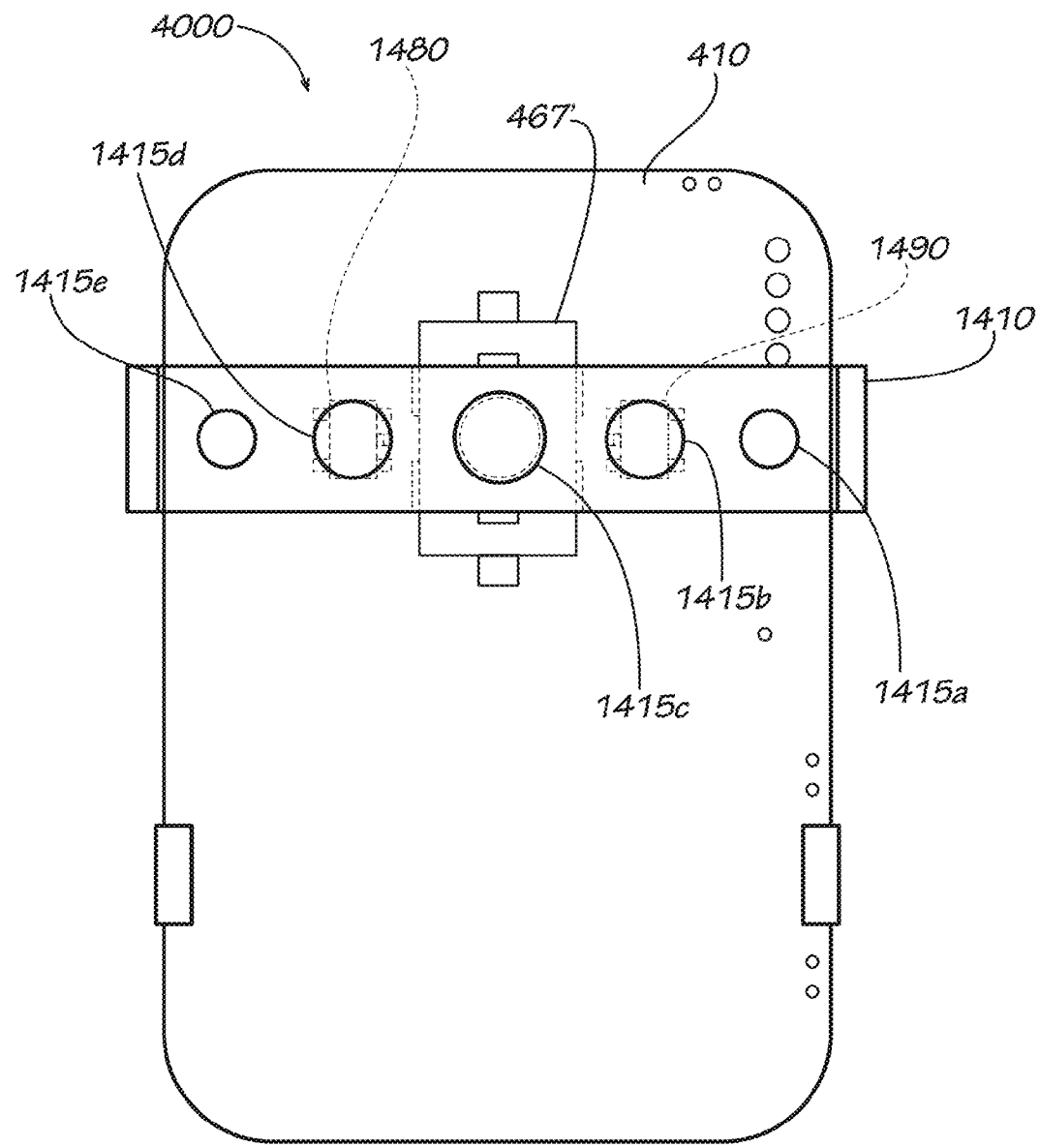
FIG. 14 is a front side view of a PCB assembly in accord with one embodiment of the current disclosure.

Another embodiment of a PCB assembly 4000 is shown in FIG. 14. The PCB assembly 4000 of the current embodiment is designed to interface with a specialized temperature probe 1410. In other embodiments of the safety indicator 100, the temperature probe is a flat metal tape. In the current embodiment, the temperature probe 1410 includes five dimples 1415*a*,*b*,*c*,*d*,*e*. The dimples 1415*a*,*b*,*c*,*d*,*e* interface with the five holes 116*a*,*b*,*c*,*d*,*e* that are the temperature aperture 115. The dimples 1415*a*,*b*,*c*,*d*,*e* protrude up from the temperature probe 1410 and into the five holes 116*a*,*b*,*c*,*d*,*e* so that the temperature probe 1410 makes more direct contact with the user's skin than with a flat tape temperature probe. Also, in the embodiment of FIG. 14, two additional temperature sensors 1480,1490 are mounted to the PCB 410. The location of the temperature sensors 1480,1490 allows them to make a quicker reading of temperature coming through the temperature probe 1410 because heat need not travel all the way to the other side of the PCB 410 to reach temperature sensors 480, 490. In some embodiments, the temperature sensors 1480, 1490 will be redundant to temperature sensors 480,490. In various embodiments, any number or placement of temperature sensors 480,490,1480,1490 may be used. It can also be seen that use detector 467' is included in the current embodiment, wherein it is placed under the temperature probe 1410 so that it interfaces with dimple 1415*c*. The use detector 467' may be placed under any dimple 1415*a*,*b*,*c*,*d*,*e*, under other parts of the temperature probe 1410, at other locations on the PCB 410, or may be omitted in various embodiments.

One feature of the safety indicator 100 is that, in the current embodiment, it does not require systems, electronic links, wireless connections, or infrastructure to implement—although such features may be added in other embodiments. Instead, in the current embodiment, it is the user's responsibility to acquire the safety indicator 100, to place the safety indicator 100 in the user's headwear, to recognize overheating alarms of the safety indicator 100, and to report overheating to a supervisor, a coach, or another individual, or to remove himself or herself from the activity causing overheating. The effect of this is to shift potential liability away from supervisors and or coaches in the organizational setting.

Additionally, because the safety indicator 100 is designed for individual use, the cost is minimal as compared to comparable systems and/or methods of monitoring outdoor exposure to heating. As such, individuals may obtain and use the safety indicator 100 for any activity, including those for which no organization is required such as jogging, cross-training, cycling, gardening, and all other outdoor or otherwise heat-intensive activities. Moreover, the safety indicator 100 does not require reporting apparatus or infrastructure, so an individual need not purchase extra equipment to implement it. The safety indicator 100 is ready for use in a user's headwear or directly on skin with adhesive—or otherwise as implemented in various embodiments—as soon as its packaging is opened.

Figure 15:
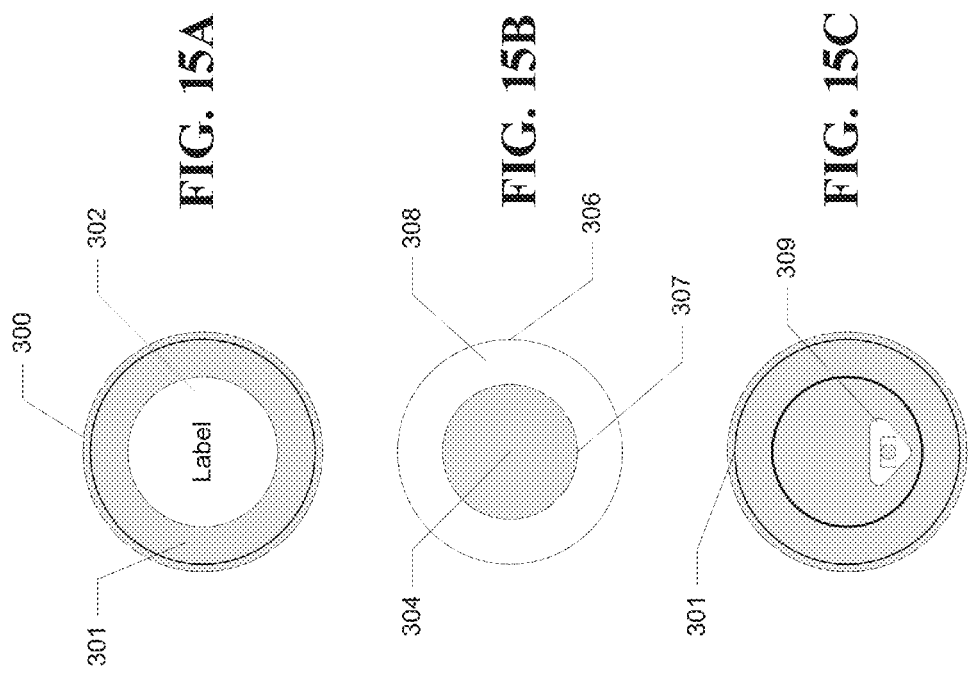
FIG. 15A is an outer side view from the front of a safety indicator in accord with one embodiment of the current disclosure.
FIG. 15B is an outer side view from the back of the safety indicator of FIG. 15A.
FIG. 15C is an outer side view from the front of the safety indicator of FIG. 15A with a label removed.
Figure 16:
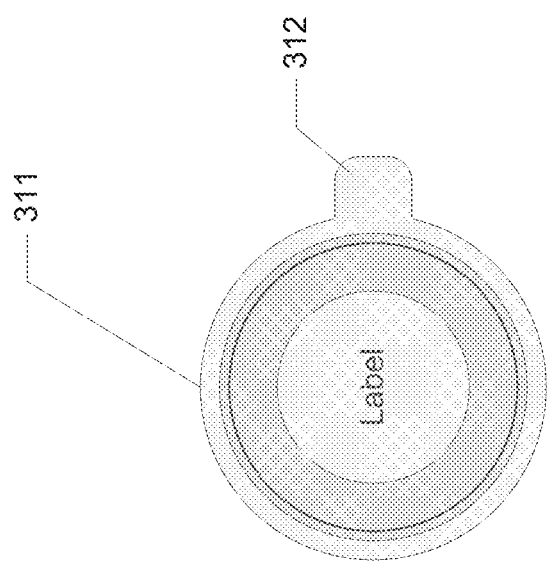
FIG. 16 is an outer side view from the front of the safety indicator of FIG. 15A with a transparent device cover included thereon.

Shown in FIGS. 15A, 15B, and 16, another embodiment of a safety indicator 300 includes the following a top enclosure 301, a bottom enclosure 304, a label 302, printed circuit board assembly (PCB assembly) 315 (seen in FIG. 17), a temperature probe, and a connection pad 308 on the reverse side 304 for mounting the device. Additionally, an optional device cover 311, used for thermal insulation, is shown in FIG. 16.

FIGS. 15A and 15B illustrate front and back views of the safety indicator 300. In the current embodiment, the shape of the safety indicator 300 is round, although in other embodiments the safety indicator 300 may be of any shape. In the current embodiment, the round shape offers flexibility for a user when it comes to mounting the safety indicator 300 on the body of a user or in headwear such as helmets. An enclosure includes the top enclosure 301 and the bottom enclosure 304. Edges of the enclosure are rounded in the current embodiment. This prevents sharp corners that may cause discomfort to a user. In various embodiments, the edges may be chamfered to facilitate user comfort and ease of mounting. As previously discussed, the safety indicator 300 may be mounted on headwear or directly on the skin of the user In the current embodiment, the top and bottom of the safety indicator 300 are made of two stamped pieces of aluminum. In the current embodiment, aluminum provides excellent thermal conductivity and is light weight. In various embodiments, various materials may be used—both thermally insulating and thermally conducting in various embodiments—to implement the enclosure. Examples of suitable thermally conductive materials include: thermally conductive plastics, polymers, titanium, stainless steel, copper, or other metal or metal alloys. Examples of suitable thermally insulating materials include: plastics, silicone, wood, resin, epoxy, foam, polymers, or various rubbers.

The aluminum top enclosure 301 and bottom enclosure 304 are press-fit together to form the enclosure. The enclosure is sealed by the press-fit process. The press-fit method is reliable and cost effective. In some embodiments, epoxy, resins, or sealants may be introduced at the joint between the top enclosure 301 and the bottom enclosure 304, although these may not be necessary in various embodiments. In the current embodiment, the enclosure is hermetically sealed to prevent contamination in the human environment in which it is intended to be used. There are however many other suitable means of mating the top enclosure 301 to the bottom enclosure 304. Such methods include: gluing, crimping, and many forms of welding. In still other variations, the enclosure can be made in one, single piece by overmolding with materials like silicone, epoxy, injection molded plastics, and various polymers. In some embodiments, the enclosure may comprise fewer or more pieces than the top enclosure 301 and the bottom enclosure 304, and one of skill in the art would understand that various joining methods may be used in various embodiments.

Figure 17:
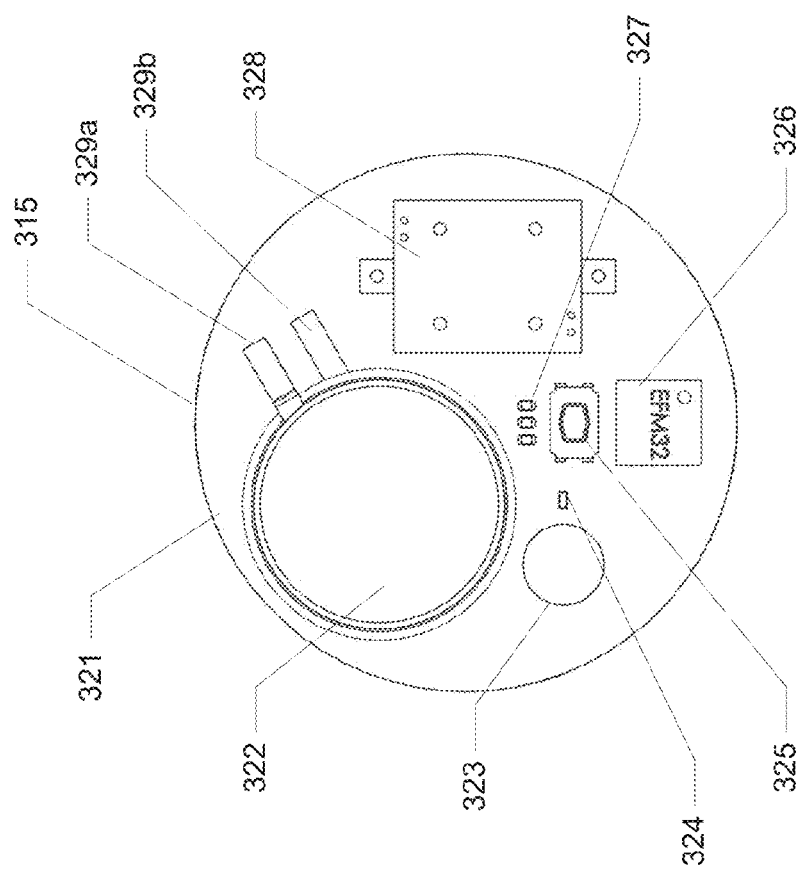
FIG. 17 is a diagram of a printed circuit board assembly of the safety indicator of FIG. 15A.

One function of the enclosure is to house and protect the PCB assembly 315 (seen in FIG. 17). In the current embodiment, the enclosure also accommodates access to any actuators, such as buttons, and allows indicators like LEDs, other lights, and audible indicators to communicate information to the user. Therefore, the top enclosure 301 has a cut-out window 309 (seen in FIG. 15C) to allow the user to press a start button, which may be a use detector in various embodiments, and to provide an opening for sound to escape in case of an audible alert. The cut-out window 309 is covered by the label 302. The label 302 both advertises the manufacturer and provides a water-tight seal over the cut-out window 309. In the current embodiment, the label 302 is a durable, sealable label affixed to the front of the top enclosure 301 such that the cut-out window 309 is sealed against introduction of water into the PCB assembly 315.

Besides serving as a protective housing of the PCB assembly 315, the enclosure also functions as the temperature probe for the current embodiment of the safety indicator 300. Because the enclosure of the current embodiment is made of thermally conductive material—in the current embodiment, aluminum—and coupled to a temperature sensor 324—in the current embodiment, a thermistor—in the PCB assembly 315, heat conducted by the enclosure can be sensed by the thermistor temperature sensor 324 and sensed by the PCB assembly 315. In various embodiments, the temperature probe may be implemented as a remote entity or a separate entity from the enclosure. In some embodiments, the temperature probe may include various configurations to mount the temperature probe to the enclosure. One of skill in the art would understand that certain features may be embodied in various arrangements, and no one configuration should be considered limiting on the disclosure.

Figure 20:
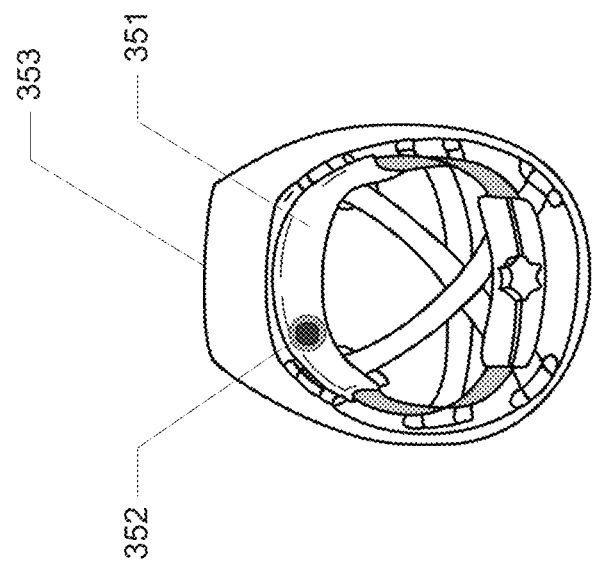
FIG. 20 is a diagram illustrating positional mounting of the safety indicator of FIG. 15A in a helmet.

In the current embodiment, the connection pad 308 is a peel-and-stick ring of medical-grade adhesive tape affixed to the reverse side of the safety indicator 300. In the current embodiment the connection pad 308 may be made of one or more of 3M Single Coated Medical Tape (Product Number 1525L), 3M Medical Nonwoven Tape (Product Number 9917), and 3M Double Coated Tapes with Adhesive 350 (Product Numbers 9500PC, 9500B, 9593, and 3028EK). In various embodiments, the adhesive may be adhesive film or adhesive. In various embodiments, the adhesive may be affixed to the safety indicator 300 during a manufacturing process or may be affixed by the user on an as-needed basis. The connection pad 308 adheres the safety indicator 300 either directly to the user's skin or to the inside of a piece of headwear such as a helmet 353 (as shown in FIG. 20), headband, or another type of headwear. The connection pad 308 of the current embodiment utilizes medical-grade adhesive to provide strong and reliable adhesion in the presence of sweat and/or personal hygiene products that may linger on the user's skin while preventing pain or harm to the user's skin upon removal. In use, the user removes an adhesive backing from the connection pad 308 before affixing the connection pad 308 to a wearable article or directly to the user's skin. In some embodiments, the connection pad 308 will be replaced by the user from time to time to ensure proper sticking and reliable temperature coupling with the user's skin.

In the case of direct skin applications, the ring shape of the connection pad 308 is but one of many shapes that would meet the requirements in alternative embodiments. In the current embodiment, the ring shape minimizes footprint while maintaining surface area in contact with the user for efficient thermal conductivity. An outer radius 306 of the connection pad 308 matches the curvature of the safety indicator 300 to minimize the footprint of the safety indicator 300 on the user's skin while still providing secure adhesion. However, an inner radius 307 of the connection pad 308 allows a thermal window as defined by the inner radius 307 for the skin to contact the enclosure directly. In the current embodiment, the enclosure is also the temperature probe, so direct contact with the skin aids in achieving a reliable temperature reading. In various embodiments, the thermal window may be omitted. In various embodiments, heat-conductive adhesive may be used to ensure proper heat transfer between the user and the safety indicator 300.

Shown in FIG. 16 is a device cover 311 that insulates the safety indicator 300 and is useful in cases of direct mounting of the safety indicator 300 to the user's skin. When the safety indicator 300 is exposed to elements such as sun, water, and wind, temperature measured at an outmost end of the safety indicator 300 may be different from the user's temperature because the enclosure is metallic and is capable of conducting heat. Exposure to the elements can act to raise the temperature of the safety indicator 300 in the case of the sun, or to lower the temperature of the safety indicator 300 in the presence of wind or water. The device cover 311 of the current embodiment also does not inhibit the functions of any actuators, buttons, or indicators like lights, LEDs, and audible alerts emanating from the safety indicator 300. In the current embodiment, the device cover 311 is made of silicone that provides thermal insulation yet is clear and thin to allow the button, LEDs, and audible alerts to function normally. In the current embodiment, the device cover 311 may be a Duro 30 type A liquid silicone rubber. In one embodiment, the device cover 311 may be NuSil MED-4930 type silicone rubber. A tab 312 extending from an edge of the device cover 311 allows the user a gripping point to remove the device cover 311 in the current embodiment. In various embodiments, the tab 312 may aid in removal of the safety indicator 300 from the user's skin or headwear.

The current embodiment of the safety indicator 300 includes the PCB assembly 315 as seen in FIG. 17. The PCB assembly 315 includes a printed circuit board (PCB) 321, a battery 322, a temperature couple 323, the temperature sensor 324, a push button 325, a microcontroller 326 and associated firmware, visual indicators 327 (LEDs in the current embodiment), and an alert indicator 328, which may be acoustic, vibrational, or both in various embodiments. In the current embodiment, the alert indicator 328 is a piezoelectric transducer. Additional support circuitry and components, including crystals, transistors, resistors, and capacitors, are not shown and would be understood by one of skill in the art to be included in the circuitry as shown.

The battery 322 includes tabs 329a,b. The tabs 329a,b are soldered to the PCB 321 like the other electronic components of the current embodiment, although various electrical connection methods would be understood by one of skill in the art as included within the scope of the disclosure. In the current embodiment, tabs 329a,b prevent the need for a separate connection mechanism to the PCB 321, allowing the safety indicator 300 to be made with a narrow profile.

The temperature couple 323 is a copper cylinder that serves as conductor of heat in the current embodiment. It extends above and below the level of the PCB 321 and is thermally coupled to both the top enclosure 301 and the bottom enclosure 304 of the enclosure. In various embodiments, the temperature couple 323 may be thermally coupled to the enclosure by thermal grease, mechanical connection, integrated construction, press-fit arrangement, or heat-conductive adhesive, among others. The temperature couple 323 is the copper cylinder in the current embodiment to provide relatively low thermal impedance from the top enclosure 301 and the bottom enclosure 304—acting as temperature probes—to the temperature sensor 324. In the current embodiment, the temperature sensor 324 is a thermistor, although various temperature sensing electronics may be used in various embodiments and may include thermocouples, mercury thermometers, and infrared sensing, among others. Coupling to both the top enclosure 301 and the bottom enclosure 304 allows the safety indicator 300 to be used in either orientation (i.e., with either of the top enclosure 301 and the bottom enclosure 304 touching the user's skin) without any loss in performance.

In the current embodiment, the temperature sensor 324 thermistor serves as one of two temperature sensors in the safety indicator 300. The other temperature sensor is built into the microcontroller 326 and serves as a redundant temperature sensor device. The temperature sensors in conjunction with the microcontroller 326 measure and evaluate the temperature of the user for the safety indicator 300.

The microcontroller 326 interprets the reading from the temperature sensor 324 thermistor, compares the reading to a reading from the internal temperature sensor of the microcontroller 326, and formulates the user's skin temperature. The push button 325 on the PCB assembly 315 activates the safety device 300, and, in the current embodiment, resets operation of the microcontroller 326 (see, e.g., FIG. 19), although various embodiments may include various functions of the push button 325, including as a use detector. In various embodiments, the push button 325 may be omitted for other use detectors as described elsewhere in this disclosure, which may include software that provides detection of use.

Different colors and modulated on/off times are used, separately or in conjunction with the audible alert and other types of alerts, to provide information to the user regarding the operational state of the safety indicator 300, a state of the battery 321, and/or the temperature condition of the user. In the current embodiment, visual alert indicators are implemented by one more LEDs 327.

The alert indicator 328, mounted to the PCB 321 serves as the audible alert to the user in the current embodiment. Like the visual alert indicators, the alert indicator 328 can be modulated to communicate different information for the user.

A connector is present on the PCB assembly 315 in some embodiments. The connector is not shown in FIG. 19. The connector allows mechanical and electrical connections for testing, programming of the microcontroller 326, and downloading of stored data in the manufacturing process. Stored data may include memory, firmware, software, or other types of electronic data. In the current embodiment the connector is not available to the user. In some embodiments, a connector may be available to the user to allow self-help software revisions, in-field firmware upgrades, downloading of logged temperature, battery charging (in the case of a rechargeable battery), and/or downloading of product usage data. In various embodiments, the connector may be a USB connector, serial connector, RCA headphone connector, or another type of connector as would be known by one of skill in the art.

Figure 18:
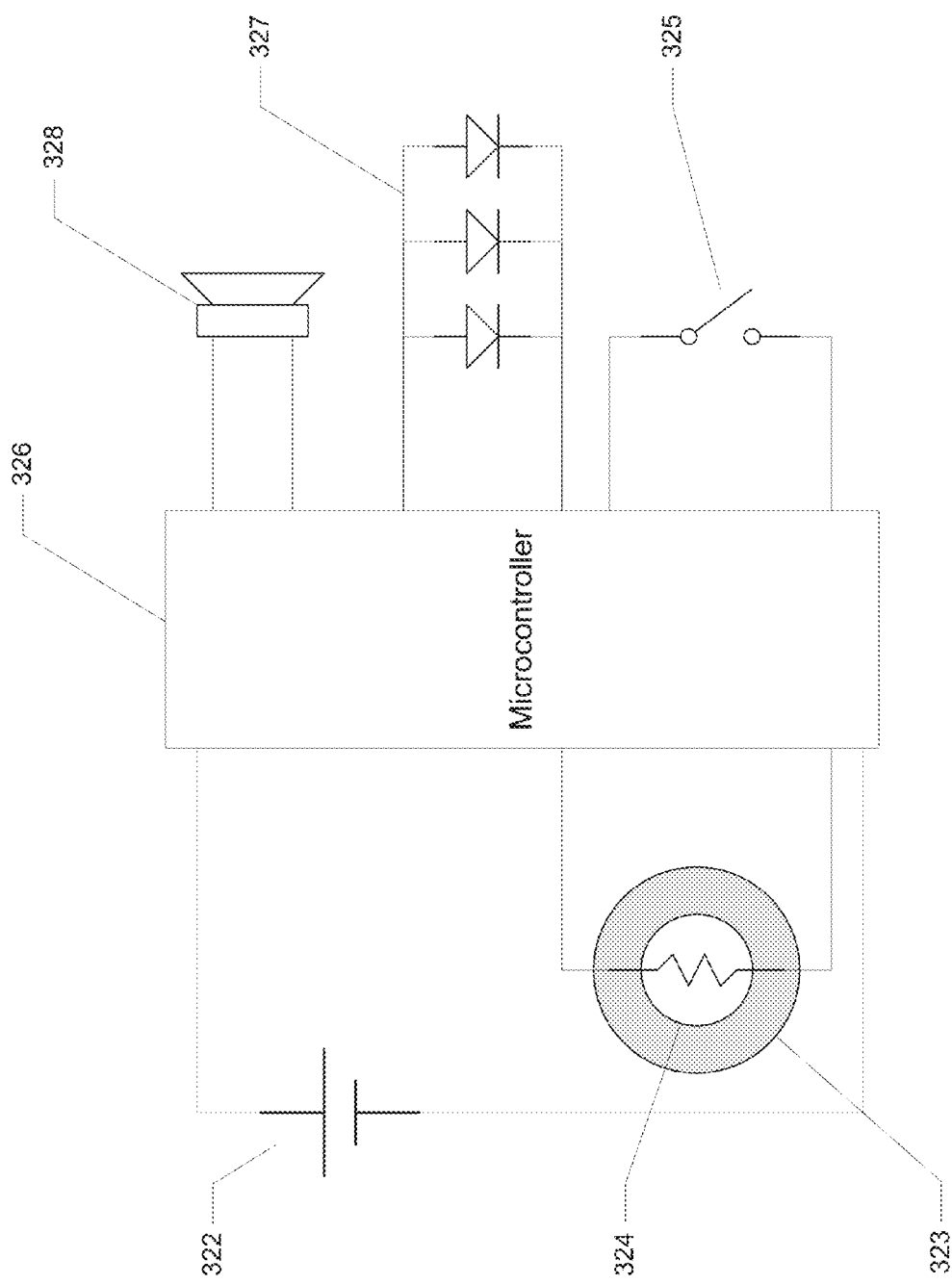
FIG. 18 is an electrical schematic diagram of the safety indicator of FIG. 15A.

An electrical schematic is seen in FIG. 18. The temperature couple 323 is shown proximate the temperature sensor 324. The signal generated is communicated to the microcontroller 326. The battery 322 in connected to supply power to the microcontroller 326, which in turn supplies power to other components connected to the microcontroller 326. The alert indicator 328 piezoelectric transducer is connected to the microcontroller 326. As previously discussed, in various embodiments, various alert indicators may be used, including various audible alert transducers. The LEDs 327 are connected to the microcontroller 326. Finally, the push button 325 is shown connected to the microcontroller 326.

Once successfully assembled and tested in manufacturing, the safety indicator 300 is ready for use. To maximize battery life, the safety indicator 300 is stored, packed, and shipped in sleep mode. In sleep mode, the safety indicator 300 uses minimum battery power until put in service by the user.

However, prior to use, the safety indicator 300 is often mounted either directly on the user's skin or in headwear such as the helmet 353, headband, or another wearable item such as an armband, shirt, pants, or other body wear to provide a measurement of body temperature of the user. In some embodiments, the safety indicator 300 may include a readout of sensed temperature in addition to other indicators.

When the user wants to mount the safety indicator 300 directly to the skin, the connection pad 308 in the current embodiment is a peel-and-stick medical-grade adhesive ring with a removable backing. Upon receiving the safety indicator 300, the user removes the backing and presses the connection pad to the user's skin in a desired location. An example of a desired anatomical location is on the forehead under a helmet 353 as shown in FIG. 21. Other desired locations include the temple, behind the ear, and various other locations. In various embodiments, temperature is easily measured at the carotid artery. Various other arteries may also serve as good locations to measure user temperature. When directly mounting, the user's skin contacts the enclosure of the safety indicator 300 directly through the access provided by the thermal window in the connection pad 308.

If the user wants to mount the safety indicator 300 into a wearable item such as the helmet 353, the same connection pad 308 supplied for the skin will suffice, but other accommodations may also be used, including adhesive covers mounting over the front of the safety indicator 300. The user may remove the backing to the connection pad 308 and press the safety indicator 300 against a headband 351 of the helmet 353 as shown in FIG. 20.

Following successful mounting, the safety indicator 300 is ready to monitor the user's temperature. When the safety indicator 300 is in operation, the temperature probe, implemented in the current embodiment by the enclosure in contact with the skin, receives heat from the user's body. The heat is conducted to the temperature sensor 324 on the PCB assembly 315 via a conduction pathway that includes the temperature couple 323 that coupled to the enclosure. The temperature sensor 324 provides a signal to the microcontroller 326 indicating the sensed temperature. In some embodiments, the signal is proportional to the user's temperature.

The microcontroller 326 then determines the user temperature (in some embodiments via calculation) and correlates that user temperature to an estimated core body temperature. For example, the difference between skin temperature measured at the temple and core body temperature is approximately 3.2° F. The estimation depends upon the physical location of the sensor on the body, and various regions various correlation factors that may be preloaded into memory of the microcontroller 326 in some embodiments. The correlation factors may be determined by testing in some embodiments or may be based on a baseline testing of a particular user with a baseline sequence.

The sensed temperature is compared to a redundant temperature sensor for error checking purposes. In the current embodiment, the temperature sensor in the microcontroller 326 may be used as previously discussed. If the temperatures are in reasonable agreement, the estimated core body temperature is relayed to the user through the visual and audible indicators. If the temperatures are out of agreement by an amount that indicates an error, an error condition is indicated to the user by the audible and visual alerts. In various embodiments, the agreement will be predetermined and loaded in the firmware of the microcontroller 326. In the current embodiment, communication through visual and audible alert indicators only indicate when the user has exceeded a threshold or when an error occurs, in which case the visual and audible alert indicators serve as a warning to the user. In various embodiments, various modifications of visual and audible alert indicators may communicate other information to the user, including the usage mode, whether the safety indicator 300 is actively monitoring, whether the safety indicator 300 has experienced an error, whether the battery is low, and the actual sensed temperature.

A state table 343 is seen in FIG. 19. If the sensed temperature at the temperature sensor 324 is within an allowable range as compared to the temperature sensor of the microcontroller 326, the temperature is validated and passes the error checking. The validated temperature measurement is used to determine a resulting core body temperature estimate. The core body temperature estimate is then classified into one of the following temperature ranges implemented as states of the device: Too Cold, Normal, Overheated, and Too Hot.

As seen with reference to FIG. 19, the comparison of the measured temperature with the following thresholds is interpreted by the microcontroller 326 as an event in the state-transition diagram. The transition points between states can be seen in FIG. 19 and are described below:

$T_{OVERHEAT}$ is the temperature at which the safety indicator 300 determines the user has overheated. When the safety indicator 300 measures the user's temperature at $T_{OVERHEAT}$, the safety indicator 300 alerts the user to inform the user that he or she is at a potentially dangerous body temperature.

$T_{RECOVERY}$ is the temperature to which the safety indicator 300 returns, or recovers, following a temperature measured at or above $T_{OVERHEAT}$. The safety indicator 300 of the current embodiment cannot re-arm to a potential alert state until $T_{RECOVERY}$ is achieved.

$T_{BIO\_MIN}$ is a minimum biologic temperature that the safety indicator 300 would expect to see when in contact with a human body. Thereby, $T_{BIO\_MIN}$ is a threshold minimum for the safety indicator 300 for the human condition. Similarly, $T_{BIO\_MAX}$ is the maximum biologic temperature that the safety indicator 300 would expect to see when in contact with a human body. Temperatures greater than $T_{BIO\_MAX}$ are determined to be out of the range of the human condition.

The safety indicator 300 functions under the control of the firmware embedded in the microcontroller 326, and according to the next-state table 343 shown in FIG. 19. The functionality of the safety indicator 300 through its next-state table is explained henceforth. As executed by the microcontroller 326, the safety indicator's 300 behavior is a function of the current state and the next event of either a button press, temperature within certain ranges, or a timeout.

In the current embodiment, the safety indicator is shipped in its sleeping state and is only awakened when the user presses the push button 325. All other events in this state are ignored. In the sleeping state, the safety indicator 300 is in a very low power mode to conserve battery life and is not measuring temperature. The safety indicator 300 will remain in this state until the battery no longer has enough energy for it to function.

Upon the button press, the safety indicator 300 performs a self-test that includes, among other internal tests, determining whether the battery 322 is functional. If all is well, the safety indicator 300 begins to measure temperature and continues execution in one of the following states: Too Cold, Normal, Overheated, or Too Hot. If there is a malfunction detected in the self-test, or a low battery state, the safety indicator 300 enters a safe state but attempts to inform the user through a series of visual and audible indications as will be discussed later.

As seen with reference to FIG. 19, the safety indicator 300 in a Sleeping state is woken by a press of the push button 325. The present state 342 of the safety indicator 300 is shown in table. In all states, a press of the push button 325 wakes the safety indicator 300. For most present states 342 of the safety indicator 300, if the sensed temperature is below $T_{BIO\_MIN}$, the safety indicator 300 goes to the Too Cold state. If the sensed temperature is between $T_{BIO\_MIN}$ and $T_{RECOVERY}$, the safety indicator 300 goes to Normal state for all present states 342 of the safety indicator 300. Then the sensed temperature is between $T_{RECOVERY}$ and $T_{OVERHEAT}$, the safety indicator 300 goes to Normal state for all present states 342 except if the safety indicator 300 is already in the Overheated state. If the safety indicator 300 is already in the Overheated state, the safety indicator 300 remains in the Overheated state (and, therefore, continues to alert the user) until $T_{RECOVERY}$ is achieved. If the sensed temperature is between $T_{OVERHEAT}$ and $T_{BIO\_MAX}$, the user is likely overheated, and the safety indicator 300 goes to the Overheated state for most present states 342. However, if the safety indicator 300 is already in the Too Hot state, the safety indicator 300 may go to Too Hot Timeout after a certain and/or predetermined amount of time. If the safety indicator 300 is already at Too Hot Timeout state, the safety indicator 300 goes to Normal state. If the sensed temperature is greater than $T_{BIO\_MAX}$, the safety indicator 300 determines that it is no longer in the human condition and moves to the Too Hot state. If the safety indicator 300 remains in the Too Hot or Too Cold states for a certain and/or predetermined amount of time, it returns to the Sleeping state. In some embodiments, the safety indicator 300 may be configured to disregard temperature readings in excess of 105.0 degrees Fahrenheit as a non-human temperature reading. This reading is termed a lockout threshold.

In some embodiments, a sensed temperature that exceeds the lockout threshold may decrease when the safety indicator 300 comes in contact with the user. For example, if the safety indicator 300 is exposed to solar radiation for an extended amount of time, the sensed temperature may exceed 105.0 degrees Fahrenheit. When the user applies the safety indicator 300, the sensed temperature will decrease because the user's temple will be at a temperature below 105.0 degrees Fahrenheit. In such cases, the safety indicator 300 may be configured to disregard temperature readings in excess of 102.5° F.—those that would normally trigger an alert—until the user temperature is sensed below 102.5° F.

In the current embodiment, the user is notified of both the state of the safety indicator 300 (e.g. battery state, wake state, sleeping state, etc.) and their body temperature state (as described with reference to FIG. 19) by a sequence of tones from the alert indicator 328 accompanied by coded flash sequences of the LEDs 327. The meaning of the codes can be disclosed to the user through accompanying product documentation (i.e. a user's manual) or labeling. An exemplary embodiment of both operational and troubleshooting indications is shown in FIGS. 22A and 22B. One of skill in the art would understand that multiple variations of indicators may be used in various embodiments, and no single example should be limiting on the disclosure.

Sensor indications are shown in the sensor indication table 370 of FIG. 22A, which shows that when the safety indicator 300 indicates it is Ready for Use 371, a single increasing volume sound is emitted and the LEDs 327 shine red, yellow, and green. When the safety indicator 300 is Going to Sleep 372, a single decreasing volume sound is emitted and the LEDs 327 shine green, yellow, and red, indicating a reverse pattern from Ready for Use 371. When in an Alert State 373, the safety indicator 300 emits a single loud audible pulse and then five warning pulses and the LEDs 327 shine red, red, and red. In various embodiments, the safety indicator 300 will repeat these indications a fixed number of times, or continuously, until the temperature state changes.

Troubleshooting indications are described with reference to the troubleshooting table 375 of FIG. 22B. When indicating Low Battery 376, the safety indicator 300 emits three loud audible pulses and the LEDs 327 shine yellow, yellow, and yellow. When indicating a Dead Battery 377, the safety indicator 300 emits a single loud audible pulse followed by three warning pulses and the LEDs shine red, red, and red before the battery 322 dies entirely. To indicate Temperature Out of Range 378 (or, as described elsewhere, outside of human condition), the safety indicator 300 emits three loud audible pulses and the LEDs 327 shine red, red, and red. Finally, when indicating a Temperature Sensor Error 379, the safety indicator 300 emits a single loud audible pulse followed by three successive decreasing volume sounds and shines five red LEDs in the current embodiment. In various embodiments, flashing LEDs 327 and various audio sounds may be used to indicate various conditions and features of the safety indicator 300, and one of skill in the art would understand that the multiple embodiments may include various configurations of such LEDs 327 and audible alerts and indicators.

It is understood that battery life of the safety indicator 300 is difficult to predict with precision and depends greatly on the amount of use and the amount of energy expended in visual and audible indicators. Therefore, the user may be exposed to an unsafe condition if he or she is actively using a safety indicator 300 with a weak battery. As such, it is a safety feature of the current embodiment to deplete any remaining electrical energy stored in the battery 322 if a low battery state is detected. In some embodiments the depletion can be triggered by a temporal event such as the calendar expiration of one year from the first activation of the safety indicator 300. When in such a depletion mode, the safety indicator 300 will not function, removing the potential for a false negative or false positive alert state detection. When the safety indicator 300 reaches depletion mode, the safety indicator 300 should be disposed by the user.

In various embodiments, the connection pad 308 used for mounting the safety indicator 300 may be implemented by other chemical or mechanical affixing means such as glue, Velcro, variations of Velcro, sewing into fabric pockets, tape, magnets, affixed by winged tabs, clips, fingers, and/or other affixing means. In various embodiments, the safety indicator 300 may be integrated into headwear prior to purchase by the end user.

In various embodiments, the activation of the safety indicator 300 can be implemented by other actuators such as a pressure sensor (indicating wear by the user), a temperature sensor checking for body versus ambient temperature, photoelectric sensor, or ambient light sensor. Various methods, apparatus, and systems described with reference to the various safety indicators 100, 100', 300 may be interchanged between the various embodiments and would be understood by one of skill in the art to embody various interchangeable and alternative designs.

Various means of anticipating the user's need to monitor temperature using the safety indicator 300 can be implemented. In the current embodiment of the safety indicator 300, a simple button is used to activate the safety indicator 300 and begin monitoring temperature. Other embodiments may omit the requirement of user action, in this case a simple button press, for an automatic starting of the safety indicator 300. The automated starting in some embodiments may come with the burdens of greater complexity, reduced reliability, greater product cost, and potentially reduced battery life of the safety indicator 300. However, automated starting may help prevent inadvertent misuse of the safety indicator 300 by a user who may forget to initiate the safety indicator 300 by the push button 325. Automatic starting may be implemented by pressure sensors, motion sensors, light sensors, or various other sensors. Moreover, in other variations, a combination of the above mentioned sensors can be used to attempt to prevent false starting of the safety indicator 300, as false starting may negatively affect battery longevity. In the current embodiment, a hybrid of push button 325 and software may be implemented to allow the user to activate the safety indicator 300 manually or automatically based on the user's temperature. It is also possible in various embodiments that no use detector will be used, and the safety indicator 300 will operate continuously.

In various embodiments, one or multiple temperature sensors may be used to increase reliability in temperature measurement. In variations of the current system, the temperature sensors may be altered or combined with additional sensors to sense other human functions including blood pressure, heart rate, and caloric data, among others.

In the current embodiment, the safety indicator 300 does not require wireless systems, electronic links, wireless connections, or infrastructure to implement, although such features may be added included in various embodiments. Instead, in the current embodiment, it is the responsibility of the user: to place the safety indicator 300 in the user's headwear or on the user's head; to recognize overheating alarms of the safety indicator 300; and to report overheating to a supervisor, a coach, or another individual or to remove himself or herself from the activity causing overheating. Because responsibility for monitoring the safety indicator 300 for alert indicators is on the individual in the current embodiment, organizations may shift potential liability away from supervisors and/or coaches in the organizational setting.

Figure 23:
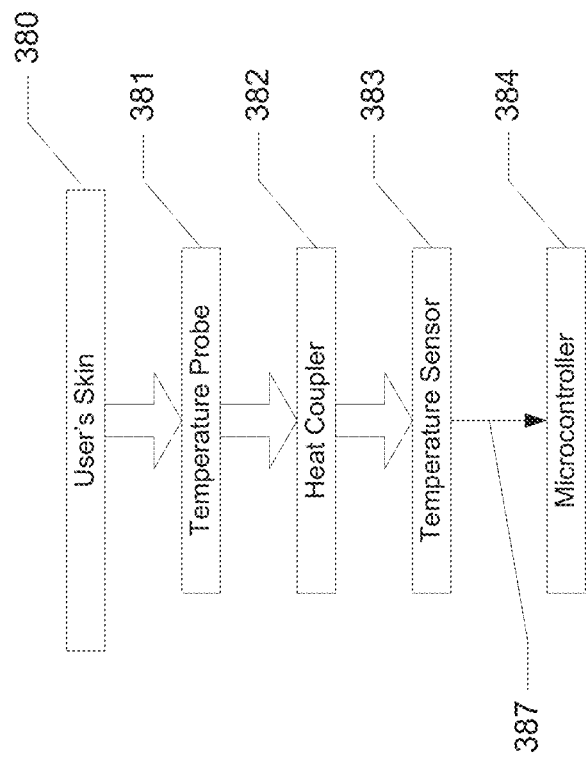
FIG. 23 is a heat conduction flow diagram of the safety indicator of FIG. 15A.

A heat pathway that ultimately results in an estimated core body temperature from the heat transferred from the user's skin is shown in FIG. 23. A temperature probe 381 (in the current embodiment, the metal enclosure) is in contact with the user's skin 380 and receives heat from the user's body. The heat is conducted to a temperature sensor 383 (temperature sensor 324 in the current embodiment) on the PCB 321 by a heat coupler 382 (temperature couple 323 in the current embodiment). The temperature sensor 383 provides an electrical signal 387 to a microcontroller 384 (microcontroller 326 in the current embodiment) proportional to the temperature. The microcontroller 384 then calculates the skin temperature and correlates that measurement to an estimated core body temperature.

In various embodiments, the safety indicator may be other types of indicators, for example, a vibration motor, a light, temperature-sensitive color-shifting material, or a wireless signal among other types of indicators. Moreover, there may be various types of indicators for each method. For example, an indicator 450 vibration motor may be a DC motor, a stepper motor, a solenoid, or any other system configured to provide vibration through electromotive force. Similarly, an indicator 450 light may be an incandescent light, an LED, or a display, among others embodiments.

It should be emphasized that the embodiments described herein are merely possible examples of implementations, merely set forth for a clear understanding of the principles of the present disclosure. Many variations and modifications may be made to the described embodiment(s) without departing substantially from the spirit and principles of the present disclosure. Further, the scope of the present disclosure is intended to cover any and all combinations and sub-combinations of all elements, features, and aspects discussed above. All such modifications and variations are intended to be included herein within the scope of the present disclosure, and all possible claims to individual aspects or combinations of elements or steps are intended to be supported by the present disclosure.

One should note that conditional language, such as, among others, "can," "could," "might," or "may," unless specifically stated otherwise, or otherwise understood within the context as used, is generally intended to convey that certain embodiments include, while alternative embodiments do not include, certain features, elements and/or steps. Thus, such conditional language is not generally intended to imply that features, elements and/or steps are in any way required for one or more particular embodiments or that one or more particular embodiments necessarily include logic for deciding, with or without user input or prompting, whether these features, elements and/or steps are included or are to be performed in any particular embodiment. Unless stated otherwise, it should not be assumed that multiple features, embodiments, solutions, or elements address the same or related problems or needs.

Various implementations described in the present disclosure may include additional systems, methods, features, and advantages, which may not necessarily be expressly disclosed herein but will be apparent to one of ordinary skill in the art upon examination of the following detailed description and accompanying drawings. It is intended that all such systems, methods, features, and advantages be included within the present disclosure and protected by the accompanying claims.

What is claimed is:

1. A human safety system comprising: a circuit including a microcontroller and at least one power source; a temperature probe in communication with the circuit, wherein the temperature probe includes a first sensor, wherein the first sensor is adapted to detect a temperature; at least one use detector in communication with the circuit, wherein the at least one use detector includes a second sensor, wherein the second sensor is adapted to detect whether the human safety system is in use by a human, and wherein the use detector is adapted to activate the human safety system when use by a human is detected by the second sensor; at least one alert indicator in communication with the circuit wherein the at least one alert indicator is adapted to signal an alert when the human safety system is activated by the at least one use detector and when a user temperature exceeds a maximum user temperature or falls below a minimum user temperature; and an adhesive with a removable backing and a replaceable connection pad, the adhesive adapted to affix an enclosure of the human safety system to one of skin and a wearable article in thermal communication with the skin.

2. The human safety system of claim 1, wherein the temperature probe is an enclosure of the human safety system.

3. The human safety system of claim 2, further comprising a temperature couple proximate the temperature probe.

4. The human safety system of claim 3, wherein the first sensor is a temperature sensor in communication with the circuit.

5. The human safety system of claim 4, wherein the temperature sensor is a thermistor proximate the temperature couple.

6. The human safety system of claim 1, wherein at least one use detector is a push button.

7. The human safety system of claim 1, wherein at least one alert indicator is an audible alert indicator.

8. The human safety system of claim 7, wherein each audible alert indicator is a piezoelectric transducer.

9. The human safety system of claim 1, wherein at least one alert indicator is a visual alert indicator.

10. The human safety system of claim 9, wherein each visual alert indicator is an LED.

11. The human safety system of claim 9, further comprising a device cover.

12. A method of using a human safety device, the method comprising: initiating operation of the human safety device, including activating a use detector; programming a maximum user temperature and a minimum user temperature, wherein the maximum user temperature is less than a maximum human condition temperature and where the minimum user temperature is greater than a minimum human condition temperature; arranging a portion of an enclosure of the human safety device in thermal communication with skin, wherein the portion of the enclosure includes a temperature probe, the temperature probe including a temperature sensor, wherein the arranging the portion of the enclosure of the human safety device in thermal communication with skin includes removing an adhesive backing from a replaceable connection pad and affixing the human safety device to one of skin and a wearable article: monitoring the human safety device for alert indicators; and signaling an alert if the user temperature exceeds the maximum user temperature or falls below the minimum user temperature.

13. The method of claim 12, further comprising the step of arranging a device cover over the human safety device.

14. The method of claim 12, further comprising the step of replacing the connection pad with a new connection pad.

15. A method of monitoring temperature of a user, the method comprising: activating a use detector; starting an internal clock, the internal clock adapted to permanently activate a human safety device after a predetermined time period, wherein the human safety device includes an adhesive with a removable backing and a replaceable connection pad, the adhesive adapted to affix an enclosure of the human safety system to one of skin and a wearable article with a portion of the enclosure in thermal communication with the skin, waking from sleep state; sensing temperature of the user; determining if the user temperature is within a human condition temperature range, the human condition temperature range including a maximum human condition temperature and a minimum human condition; continuously monitoring a user temperature such that an increase in the user temperature above a maximum user temperature or a decrease in the user temperature below a minimum user temperature-triggers an alert, wherein the maximum user temperature is less than the maximum human condition temperature and where the minimum user temperature is greater than the minimum human condition temperature; and, returning to sleep state when the user temperature is above the maximum human condition temperature or below the minimum human condition temperature for a predetermined amount of time.

16. The method of claim 15, further comprising the step of alerting the user if the sensed temperature is unsafe.

17. The method of claim 16, wherein the user is alerted if the sensed temperature is greater than a predetermined overheat temperature.

18. The method of claim 17, wherein the user is alerted until the temperature falls below a recovery temperature.

19. The method of claim 15, wherein the human condition is defined between a predetermined minimum bio temperature and a predetermined maximum bio temperature.

* * * * *